US007910647B2

(12) United States Patent
Weide et al.

(10) Patent No.: US 7,910,647 B2
(45) Date of Patent: Mar. 22, 2011

(54) ADHESION INHIBITION OF MICROORGANISMS BY NON-IONIC SURFACTANTS

(75) Inventors: Mirko Weide, Duesseldorf (DE); Stefan Frey, Daldesheim (DE); Juergen Stodt, Neuss (DE); Andreas Bolte, Duesseldorf (DE); Roland Breves, Mettmann (DE); Thomas Gerke, Neuss (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 337 days.

(21) Appl. No.: 11/450,859

(22) Filed: Jun. 8, 2006

(65) Prior Publication Data

US 2006/0257281 A1 Nov. 16, 2006

Related U.S. Application Data

(63) Continuation of application No. PCT/EP2004/013038, filed on Nov. 17, 2004.

(30) Foreign Application Priority Data

Dec. 13, 2003 (DE) .................................. 103 58 534

(51) Int. Cl.
B08B 17/00 (2006.01)

(52) U.S. Cl. ............................................ 524/379; 422/6

(58) Field of Classification Search ......... 422/6; 524/379
See application file for complete search history.

(56) References Cited

U.S. PATENT DOCUMENTS

| 3,234,258 | A |   | 2/1966  | Morris        |         |
|-----------|---|---|---------|---------------|---------|
| 3,393,164 | A | * | 7/1968  | Braun         | 524/588 |
| 3,632,557 | A |   | 1/1972  | Brode et al.  |         |
| 3,920,586 | A | * | 11/1975 | Bonaparte et al. | 510/349 |
| 3,971,751 | A |   | 7/1976  | Isayama et al. |        |
| 3,979,344 | A |   | 9/1976  | Bryant et al. |         |
| 4,060,844 | A |   | 11/1977 | Davis         |         |
| 4,176,102 | A | * | 11/1979 | Favata        | 524/60  |
| 4,277,387 | A | * | 7/1981  | Jordan et al. | 524/292 |
| 4,417,042 | A |   | 11/1983 | Dziark        |         |
| 4,503,210 | A |   | 3/1985  | Von Au et al. |         |
| 4,537,944 | A | * | 8/1985  | Imai et al.   | 528/18  |
| 4,632,847 | A | * | 12/1986 | Lomasney et al. | 588/249 |
| 4,664,839 | A |   | 5/1987  | Rieck         |         |
| 4,871,594 | A |   | 10/1989 | Bister et al. |         |
| 4,891,400 | A |   | 1/1990  | Schwabe et al. |        |
| 4,900,773 | A | * | 2/1990  | Hartschen et al. | 524/473 |
| 4,910,242 | A | * | 3/1990  | Podola et al. | 524/158 |
| 4,912,153 | A |   | 3/1990  | Jeremias et al. |       |
| 4,942,211 | A |   | 7/1990  | Sommer et al. |         |
| 4,967,017 | A | * | 10/1990 | Schmid et al. | 568/621 |
| 5,016,711 | A | * | 5/1991  | Cowan         | 166/293 |
| 5,047,249 | A | * | 9/1991  | Rothman et al. | 424/543 |
| 5,075,041 | A |   | 12/1991 | Lutz          |         |
| 5,077,360 | A |   | 12/1991 | DePompei et al. |       |
| 5,091,447 | A | * | 2/1992  | Lomasney      | 523/408 |
| 5,226,954 | A | * | 7/1993  | Suzuki        | 106/2   |
| 5,262,007 | A | * | 11/1993 | Phan et al.   | 162/158 |
| 5,356,607 | A |   | 10/1994 | Just          |         |
| 5,378,406 | A |   | 1/1995  | Nagaoka       |         |
| 5,412,015 | A | * | 5/1995  | Sommer et al. | 524/425 |
| 5,502,144 | A |   | 3/1996  | Kuo et al.    |         |
| 5,525,120 | A |   | 6/1996  | Zauns-Huber et al. |    |
| 5,525,654 | A |   | 6/1996  | Podola et al. |         |
| 5,670,557 | A | * | 9/1997  | Dietz et al.  | 522/184 |
| 5,705,169 | A |   | 1/1998  | Stein et al.  |         |
| 5,730,960 | A |   | 3/1998  | Stein et al.  |         |
| 5,767,054 | A |   | 6/1998  | Sprugel et al. |        |
| 5,780,043 | A |   | 7/1998  | Dane et al.   |         |
| 5,780,420 | A |   | 7/1998  | Bruer et al.  |         |
| 5,880,299 | A |   | 3/1999  | Ponsati Obiols et al. |  |
| 5,945,091 | A |   | 8/1999  | Habeck et al. |         |
| 6,025,416 | A |   | 2/2000  | Proebster et al. |      |
| 6,162,756 | A |   | 12/2000 | Friebe et al. |         |
| 6,168,808 | B1 |  | 1/2001  | Godin et al.  |         |
| 6,184,274 | B1 |  | 2/2001  | Herold et al. |         |
| 6,187,327 | B1 |  | 2/2001  | Stack         |         |
| 6,193,960 | B1 |  | 2/2001  | Metzger et al. |        |
| 6,207,720 | B1 | * | 3/2001 | Maeda et al.  | 516/73  |
| 6,225,398 | B1 | * | 5/2001 | Boudreaux et al. | 524/507 |
| 6,235,124 | B1 |  | 5/2001  | Rubin         |         |
| 6,303,678 | B1 | * | 10/2001 | Ziche et al. | 524/379 |
| 6,491,840 | B1 | * | 12/2002 | Frankenbach et al. | 252/8.91 |
| 6,503,994 | B1 | * | 1/2003 | Nehren et al. | 528/17  |
| 6,677,293 | B1 |  | 1/2004  | Allgaier et al. |       |
| 6,699,930 | B1 | * | 3/2004 | Schmidt et al. | 524/588 |
| 6,822,021 | B1 | * | 11/2004 | Kim et al.   | 523/216 |
| 2002/0073667 | A1 |    | 6/2002 | Barris et al. |        |
| 2004/0044138 | A1 | * | 3/2004 | Aranguiz et al. | 525/314 |
| 2004/0266634 | A1 | * | 12/2004 | Bockmuhl et al. | 510/101 |
| 2005/0136251 | A1 | * | 6/2005 | Kishimoto et al. | 428/343 |

FOREIGN PATENT DOCUMENTS

| AT | 395415 B    | 5/1992  |
|----|-------------|---------|
| CA | 2 078 787   | 9/1991  |
| CA | 1 294 724   | 1/1992  |
| DE | 2031109     | 12/1971 |
| DE | 36 02 526 A1 | 7/1987 |
| DE | 37 26 547 A1 | 2/1989 |
| DE | 40 09 095 A1 | 9/1991 |
| DE | 40 29 504 A1 | 3/1992 |
| DE | 42 33 077 A1 | 4/1994 |
| DE | 43 01 553 A1 | 7/1994 |

(Continued)

OTHER PUBLICATIONS

Database WPI Section Ch, Week 20004, Derwent Publications Ltd., London GB; AN 2005-033862, XP002322055 for JP 2004 346124 (2004).

(Continued)

Primary Examiner — Randy Gulakowski
Assistant Examiner — Robert Loewe
(74) Attorney, Agent, or Firm — James E. Piotrowski; Steven C. Bauman

(57) ABSTRACT

Non-ionic surfactants are used to reduce the adhesion of microorganisms to surfaces of materials by coating such surfaces with the surfactants or incorporating the surfactants into the materials.

20 Claims, No Drawings

FOREIGN PATENT DOCUMENTS

| | | |
|---|---|---|
| DE | 44 00 024 A1 | 7/1995 |
| DE | 195 39 846 C1 | 11/1996 |
| DE | 195 49 425 A1 | 3/1997 |
| DE | 197 04 553 A1 | 8/1998 |
| DE | 197 12 033 A1 | 9/1998 |
| DE | 698 05 697 T2 | 12/2002 |
| EP | 0 118 030 A1 | 9/1984 |
| EP | 0 164 514 A1 | 12/1985 |
| EP | 0 227 108 A2 | 7/1987 |
| EP | 0286008 A2 | 10/1988 |
| EP | 0 316 591 A2 | 5/1989 |
| EP | 0341151 A2 | 11/1989 |
| EP | 0 370 464 A2 | 5/1990 |
| EP | 0 327 847 B1 | 1/1994 |
| EP | 0 553 143 B1 | 5/1995 |
| EP | 0 728 749 A2 | 8/1996 |
| EP | 0 693 471 B1 | 1/1998 |
| EP | 0 694 521 B1 | 1/1998 |
| EP | 0 818 450 A1 | 1/1998 |
| EP | 0 670 674 B1 | 4/1998 |
| EP | 0 824 574 B1 | 10/1999 |
| EP | 0 703 292 B1 | 4/2001 |
| EP | 1 094 065 A2 | 4/2001 |
| EP | 1229091 A2 | 8/2002 |
| GB | 2 211 093 A | 6/1989 |
| JP | 61-42586 * | 1/1986 |
| WO | WO 88/06038 A1 | 8/1988 |
| WO | WO 91/08171 A1 | 6/1991 |
| WO | WO 93/005089 A1 | 3/1993 |
| WO | WO 95/07331 A1 | 3/1995 |
| WO | WO 95/15182 A1 | 6/1995 |
| WO | 9626783 A1 | 9/1996 |
| WO | WO 97/04768 A1 | 2/1997 |
| WO | 9724290 A1 | 7/1997 |
| WO | WO 00/12660 A2 | 3/2000 |
| WO | WO 00/68232 A1 | 11/2000 |
| WO | WO 01/09249 A1 | 2/2001 |
| WO | WO 03/051124 A2 | 6/2003 |
| WO | WO-03/051126 A1 * | 6/2003 |

OTHER PUBLICATIONS

Du et al., "Grafted poly-(ethylene glycol) on lipid surfaces inhibits protein adsorption and cell adhesion", *Biochimica et Biophysica Acta* 1326 pp. 236-248 (1997).

Harder et al., "Molecular Conformation in Oligo(ethylene glycol)-Terminated Self-Assembled Monolayer on Gold and Silver Surfaces Determines Their Ability to Resist Protein Adsorption", *J. Phys. Chem. B*, 102, pp. 426-436 (1998).

Prime et al., "Adsorption of Proteins onto Surfaces Containing End-Attached Oligo(ethylene oxide): A Model System Using Self-Assembled Monolayers", *J. Am. Chem. Soc.*, 115, pp. 10714-10721 (1993).

Cunliffe et al., "Bacterial Adhesion at Synthetic Surfaces", *Appl Environ Microbiol*, vol. 65 (11), pp. 4995-5002 (1999).

Die von Paster et al., "Bacterial Diversity in Human Subgingival Plaque", *Journal of Bacteriology*, vol. 183 (12), pp. 3770-3783 (2001).

"Sealants—Jointing products in building constructions", DIN EN 26927, Beuth Verlag GmbH, Berlin pp. 1-5, May 1991.

"Sample Preparation for Trace Analysis to Sintered Steel and Iron", *Ulmann's Encyclopedia of Industrial Chemistry*, 6$^{th}$ Edition, vol. 32, Chapter 4 (2003).

P. Finkel, "Formulierung kosmetischer Sonnenschutzmittel", *SOFW-Journal*, vol. 122, pp. 543-548 (199.

* cited by examiner

ADHESION INHIBITION OF MICROORGANISMS BY NON-IONIC SURFACTANTS

CROSS-REFERENCE TO RELATED APPLICATIONS

This application is a continuation under 35 U.S.C. §365(c) and 35 U.S.C. §120 of international application PCT/EP2004/013038, filed Nov. 17, 2004, and published Jun. 23, 2005, as WO 2005/056741, incorporated herein by reference in its entirety. This application also claims priority under 35 U.S.C. §119 of DE 10358534.6, filed Dec. 13, 2003, which is incorporated herein by reference in its entirety.

FIELD OF THE INVENTION

The invention relates to the use of non-ionic surfactants for the reduction of adhesion of microorganisms on surfaces, to compositions, preparations and materials that comprise these substances or are coated with these substances.

DISCUSSION OF THE RELATED ART

There is a need in the most diverse areas for agents that prevent the adhesion of microorganisms.

In households for example, mold is found in many different places such as in the kitchen or in moist areas such as, for example in the bathroom. Molds give rise to significant problems because the spores released by them into the atmosphere are often the cause of allergies. Combating such fungi with biocides involves an increased risk of bocidal resistance, such that after some time new antimicrobials have to be found which are effective against these resistant microorganisms. Furthermore, biocides are not always ecologically and toxicologically harmless.

Moreover, delicate textiles, such as e.g., microfibers, are more and more frequently used for clothing that may only be washed at 30 or 40° C. Consequently, fungi, such as for example the human pathogen *Candida albicans*, are not destroyed. Particularly after a fungal infection, such fungi that have not been destroyed but which adhere to clothing can cause a re-infection.

In addition, wearers of dentures frequently contract an oral candidosis (moniliosis). Fungus cells that adhere to the surface of the prosthesis can, through contact, colonize the mucous membranes that are often already damaged by ulcers.

Up to now, antimicrobials that either inhibit the growth of microorganisms (biostatica) or destroy them (biocides) have been employed to prevent any re-infection from microorganisms that adhere to clothing or to plastic surfaces. This is disadvantageous, as such biocides or biostatica employed in detergents and cleansing agents pollute the waste water and thereby impair the operations of the microbial purification steps in waste water treatment plants. In addition, the selective pressure on microorganisms strongly increases their resistance, such that after some time new antimicrobials have to be found which are effective against these resistant microorganisms.

Moreover, the reduction in adhesion by reducing contact of the human body with the microorganisms, for example in the respiratory system with mold spores, can also lead to a reduction of the allergy triggering potential.

BRIEF SUMMARY OF THE INVENTION

Accordingly, the object of the present invention is to selectively remove microorganisms from surfaces, without polluting these surfaces or the wastewater with biocides and/or biostatica.

This object is achieved by the use of non-ionic surfactants to reduce the adhesion of microorganisms on surfaces.

It is already known that polyethylene glycol groups can prevent adsorption on certain surfaces if they are covalently fixed on the surfaces in question. However, the processes described for fixing the polyethylene glycol groups are very involved and additionally have long been limited to commercially uninteresting surfaces and/or are difficult to realize in practice. Thus, the coating of glass surfaces with lipid layers, and the subsequent incorporation of polyethylene glycol-modified fats in the lipid layers in order to prevent the adsorption of specific proteins and blood cells, was described by Du et al. (Biochimica et Biophysica Acta 1326, 236-248 (1997). Polyethylene glycol groups were also deposited on substrate surfaces by means of self-organizing lipid monolayers. In this context, the coating of silver and gold surfaces with n-alkane thiols that carry oligoethylene glycol units to prevent protein adsorption is described (Harder et al. (1998) J. Phys. Chem. B 102, 426-436; Prime et al. (1993) J. Am. Chem. Soc. 115, 10714-10721). Cunliffe et al. (1999; Appl Environ Microbiol. 65 (11): 4995-5002) describe the coating of silicate surfaces with functional groups that comprise amino groups, and the subsequent coupling of polyethylene glycol-containing groups onto these functional groups in order to prevent the adsorption of bacteria and proteins. The cited processes are very costly and suitable to only a limited extent in practice. Moreover, the described processes are limited to surfaces that are only of minor commercial interest. Thus, with the described processes, none of the above-cited commercially interesting surfaces, such as plastic and textile surfaces, can be treated against the adhesion of microorganisms.

Surprisingly, it has now been found that the adhesion of microorganisms to surfaces can be reduced in a simple way by means of non-ionic surfactants that do not need to be covalently fixed to the surface. This can be achieved, for example, by incorporating them in a cleaning agent or in a treatment agent, which will be used to treat the surface in question. In a particularly preferred embodiment, however, the non-ionic surfactants are incorporated and/or blended into the material, whose surface is intended to be protected against adhesion.

Accordingly, the subject matter of the present invention is a method for reducing the adhesion of microorganisms to surfaces, wherein the non-ionic surfactants are incorporated into the material or deposited on the material, the deposition and/or the incorporation preferably occurring non-covalently.

DETAILED DESCRIPTION OF CERTAIN EMBODIMENTS OF THE INVENTION

Microorganisms are understood to mean in particular bacteria, fungi as well as viruses and algae. This includes bacterial endospores and exospores as well as spores that serve as reproduction structures in fungi.

Reducing the adhesion is understood to mean a significant reduction of the number of adhering microorganism cells. Thus, the adhesion is preferably reduced by more than 20 or 40%, particularly preferably by more than 60 or 80%, in particular by more than 90 or 95%, with respect to an untreated control sample. Ideally, the adhesion is completely or almost completely prevented.

According to a particularly preferred embodiment, the non-ionic surfactants are employed in such final concentrations that they do not act as biocides or biostatica. A particular advantage of this embodiment is that the risk of resistance development against the used products is low as the microorganisms are neither killed off nor is their growth inhibited.

The concentrations, for which no growth inhibition occurs, as well as the minimum inhibition concentration itself, can be easily determined by methods known to the person skilled in the art. It could be determined experimentally that inventively preferred non-ionic surfactants showed no fungicidal action, even when used in relatively high concentrations.

Moreover, as far as is presently known, the majority of non-ionic surfactants are harmless, also from the toxicological point of view.

A further advantage of the invention is that some non-ionic surfactants, even in comparison with conventional biocides or biostatica, are already effective in low final concentrations, such that only little substance needs to be used.

A further subject matter of the present invention are compositions, preparations and materials that comprise non-ionic surfactants and/or are coated or treated with non-ionic surfactants, preferably concerning alkoxylated, principally ethoxylated and/or propoxylated surfactants, wherein a degree of ethoxylation of 5 to 15 is preferred, and wherein the non-ionic surfactants may also be fluorinated.

The compositions, preparations and materials can concern filter media, adhesives, building materials, building auxiliaries, textiles, furs, paper, hides, leather, detergents, cleansing agents, rinsing agents, hand detergents, hand dishwashing agents, automatic dishwasher agents, cosmetic preparations, pharmaceutical preparations as well as agents for the treatment or care of surfaces, building materials, filter media, building auxiliaries, ceramics, plastics, textiles, furs, paper, hides, leather or packaging, particularly those that come into contact with foodstuffs.

According to a particularly preferred embodiment, the adhesion of microorganisms to filter media, adhesives, building materials and/or building auxiliaries is reduced.

According to a further preferred embodiment, the adhesion of microorganisms on the surfaces that often come into contact with the human body is reduced. Here, in particular, are meant abiotic, industrial (or industrially manufactured) surfaces. In the scope of this particular embodiment, human or animal tissue are therefore understood not to be included.

According to a further preferred embodiment, the adhesion of microorganisms on such surfaces like textiles, ceramics, metals and/or plastics, is reduced. This particularly concerns washing, sanitary devices, screed, shoes, leather, commodities made from rubber, prosthetics or dentures.

In the cited applications, the non-ionic surfactants are advantageously deposited on the material or incorporated or blended into the material, without being covalently fixed to the surface.

The reduction in adhesion to textiles or plastic surfaces reduces the risk of a re-infection of the affected body region. The reduction in adhesion of microorganisms to ceramics, plastics or metals, particularly prosthetics or dentures, diminishes the risk of infection or re-infection, without polluting the skin, the mucous membranes or the waste water with biocidally or biostatically or virostatically active substances. By the same token, catheters as well as other medical instruments manufactured from plastics or metals, and/or prosthetics, can be freed of adhesion by the use of non-ionic surfactants, for example, in rinse or cleansing agents.

Dentures, particularly sets of teeth, can be effectively treated to reduce the adhesion of microorganisms by the use of non-ionic surfactants in mouth, tooth and or denture care products, simply and without stressing the treated surface with strongly active biocides, potentially even proven toxic substances.

Non-Ionic Surfactants

The added non-ionic surfactants preferably include alkoxylated, advantageously ethoxylated and/or propoxylated, particularly primary alcohols having preferably 8 to 22 carbon atoms, particularly 8 to 18 carbon atoms, and an average of 1 to 20, preferably 1 to 12 moles alkylene oxide, particularly preferably 5 to 15 moles alkylene oxide, advantageously ethylene oxide (EO), per mole alcohol, in which the alcohol group can be linear or preferably methyl-branched in the 2-position or can comprise linear and methyl branched groups in the mixture, as typically occur in oxo-alcohol groups. Particularly preferred are, however, alcohol ethoxylates with linear groups from alcohols of natural origin with 12 to 18 carbon atoms, e.g., from coco-, palm-, tallow- or oleyl alcohol, and an average of 2 to 8 EO or 5 to 15 EO per mole alcohol. Exemplary preferred ethoxylated alcohols include $C_{12-14}$-alcohols with 3 EO or 4 EO, $C_{9-11}$-alcohols with 7 EO, $C_{13-15}$-alcohols with 3 EO, 5 EO, 7 EO or 8 EO, $C_{12-18}$-alcohols with 3 EO, 5 EO or 7 EO and mixtures thereof, as well as mixtures of $C_{12-14}$-alcohols with 3 EO and $C_{12-18}$-alcohols with 5 EO. The cited degrees of ethoxylation constitute statistically average values that can be a whole or a fractional number for a specific product. Preferred alcohol ethoxylates have a narrowed homolog distribution (narrow range ethoxylates, NRE). In addition to these non-ionic surfactants, fatty alcohols with more than 12 EO can also be used. Examples of these are tallow fatty alcohol with 14 EO, 25 EO, 30 EO or 40 EO.

In addition, substances commonly known to the person skilled in the art as non-ionic emulsifiers can also be considered as non-ionic surfactants. In this context, the non-ionic surfactants comprise, e.g., a polyol group, a polyether group, a polyamine group or a polyamide group or a combination of the above groups as the hydrophilic group. Such compounds are, for example, addition products of $C_8$-$C_{22}$-alkyl- mono- and -oligo glycosides and their ethoxylated analogs, addition products of 2 to 30 moles ethylene oxide and/or 0 to 10, particularly 0 to 5 moles propylene oxide to fatty alcohols with 8 to 22 carbon atoms, to fatty acids with 12 to 22 carbon atoms, and to alkyl phenols with 8 to 15 carbon atoms in the alkyl group, $C_{12}$-$C_{22}$-fatty acid mono- and diesters of addition products of 1 to 30 moles ethylene oxide on glycerin as well as addition products of 5 to 60 moles ethylene oxide on castor oil and on hydrogenated castor oil.

Weakly foaming non-ionic surfactants that possess alternating ethylene oxide and alkylene oxide units can also be employed. Among these, the surfactants with EO-AO-EO-AO blocks are again preferred, wherein one to ten EO or AO groups respectively are linked together, before a block of the other groups follows. Examples of these are surfactants of the general formula

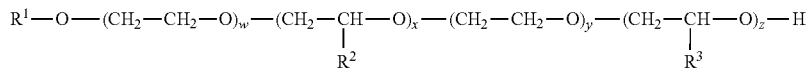

in which $R^1$ stands for a linear or branched, saturated or mono- or polyunsaturated $C_{6-24}$-alkyl or alkenyl group, each group $R^2$ or $R^3$ independently of one another is selected from —CH$_3$, —CH$_2$CH$_3$, —CH$_2$CH$_2$—CH$_3$, —CH(CH$_3$)$_2$, and the indices w, x, y, z independently of one another stand for whole numbers from 1 to 6. They can be manufactured by known methods from the corresponding alcohols R$^1$—OH and ethylene- or alkylene oxide. The group R$^1$ in the previous formula can vary depending on the origin of the alcohol. When natural sources are used, the group R$^1$ has an even number of carbon atoms and generally is not branched, the linear alcohols of natural origin with 12 to 18 carbon atoms, for example coconut, palm, tallow or oleyl alcohol, being preferred. The alcohols available from synthetic sources are, for example, Guerbet alcohols or mixtures of methyl branched in the 2-position or linear and methyl branched groups, as are typically present in oxo alcohols. Independently of the type of alcohol employed for the manufacture of the non-ionic surfactants comprised in the agents, inventive agents are preferred, wherein R$^1$ in the previous formula stands for an alkyl radical with 6 to 24, preferably 8 to 20, particularly preferably 9 to 15 and particularly 9 to 11 carbon atoms. In addition to propylene oxide, especially butylene oxide can be the alkylene oxide unit that alternates with the ethylene oxide unit in the non-ionic surfactants. However, other alkylene oxides are also suitable, in which R$^2$ or R$^3$ independently of one another are selected from —CH$_2$CH$_2$CH$_3$ or —CH(CH$_3$)$_2$.

In addition, non-ionic block copolymers are considered as non-ionic surfactants, such as, for example, those described in U.S. Pat. No. 6,677,293, incorporated herein by reference in its entirety. Here, for example, they can concern AB-, AA'B-, ABB'-, ABA'- or BAB'-block copolymers, wherein A and A' stand for a hydrophilic block and B and B' for a hydrophobic block. The blocks A and A', independently of one another can be a polyalkylene oxide, particularly a polypropylene oxide or polyethylene oxide, polyvinyl pyridine, polyvinyl alcohol, polymethyl vinyl ether, polyvinyl pyrrolidine or a polysaccharide. The blocks B and B', independently of one another, can be for example an optionally substituted alkyl group that can be obtained for example by polymerizing units selected from the group consisting of 1,3-butadiene, isoprene, all isomers of dimethylbutadiene, 1,3-pentadiene, 2,4-hexadiene, α-methylstyrene, isobutylene, ethylene, propylene or styrene or mixtures thereof. The molecular weights of the blocks A, A', B and B' are preferably, independently of one another, between 500 and 50,000 g/mole. According to the invention, at least one of the blocks A and A' is preferably an alkylene oxide.

Another class of preferred non-ionic surfactants which may be used, either as the sole non-ionic surfactant or in combination with other non-ionic surfactants are alkoxylated, preferably ethoxylated or ethoxylated and propoxylated fatty acid alkyl esters preferably containing 1 to 4 carbon atoms in the alkyl chain, in particular fatty acid methyl esters.

Furthermore, as additional non-ionic surfactants, alkyl glycosides that satisfy the general Formula RO(G)$_x$ can also be added, where R means a primary linear or methyl-branched, particularly 2-methyl-branched, aliphatic group containing 8 to 22 and preferably 12 to 18 carbon atoms and G stands for a glycose unit containing 5 or 6 carbon atoms, preferably glucose. The degree of oligomerization x, which defines the distribution of monoglycosides and oligoglycosides, is any number between 1 and 10, preferably between 1.2 and 1.4.

Non-ionic surfactants of the amine oxide type, for example N-cocoalkyl-N,N-dimethylamine oxide and N-tallow alkyl-N,N-dihydroxyethylamine oxide, and the fatty acid alkanolamides, may also be suitable.

Other suitable surfactants are polyhydroxyfatty acid amides corresponding to the following formula,

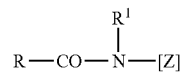

in which RCO stands for an aliphatic acyl group with 6 to 22 carbon atoms, R$^1$ for hydrogen, an alkyl or hydroxyalkyl group with 1 to 4 carbon atoms and [Z] for a linear or branched polyhydroxyalkyl group with 3 to 10 carbon atoms and 3 to 10 hydroxy groups. The polyhydroxyfatty acid amides are known substances, which may normally be obtained by reductive amination of a reducing sugar with ammonia, an alkylamine or an alkanolamine and subsequent acylation with a fatty acid, a fatty acid alkyl ester or a fatty acid chloride.

The group of polyhydroxyfatty acid amides also includes compounds corresponding to the formula,

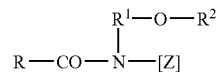

in which R is a linear or branched alkyl or alkenyl group containing 7 to 12 carbon atoms, R$^1$ is a linear, branched or cyclic alkyl group or an aryl group containing 2 to 8 carbon atoms and R$^2$ is a linear, branched or cyclic alkyl group or an aryl group or an oxyalkyl group containing 1 to 8 carbon atoms, C$_{1-4}$ alkyl or phenyl groups being preferred, and [Z] is a linear polyhydroxyalkyl group, of which the alkyl chain is substituted by at least two hydroxy groups, or alkoxylated, preferably ethoxylated or propoxylated derivatives of that group.

[Z] is preferably obtained by reductive amination of a reduced sugar, for example glucose, fructose, maltose, lactose, galactose, mannose or xylose. The N-alkoxy- or N-aryloxy-substituted compounds may then be converted into the required polyhydroxyfatty acid amides by reaction with fatty acid methyl esters in the presence of an alkoxide as catalyst.

Further usable non-ionic surfactants are the end capped poly(oxyalkylated) surfactants of the formula

in which R$^1$ and R$^2$ stand for linear or branched, saturated or unsaturated, aliphatic or aromatic hydrocarbon groups with 1 to 30 carbon atoms, R$^3$ stands for H or for a methyl, ethyl, n-propyl, isopropyl, n-butyl, 2-butyl or 2-methyl-2-butyl group, x stands for values between 1 and 30, k and j for values between 1 and 12, preferably 1 to 5. Each R$^3$ in the above formula can be different for the case where x≧2. R$^1$ and R$^2$ are preferably linear or branched, saturated or unsaturated, aliphatic or aromatic hydrocarbon groups containing 6 to 22 carbon atoms, groups containing 8 to 18 carbon atoms being particularly preferred. H, —CH$_3$ or —CH$_2$CH$_3$ are particularly preferred for the radical R$^3$. Particularly preferred values for x are in the range from 1 to 20 and more particularly in the range from 6 to 15.

In a particularly preferred embodiment, the non-ionic surfactants are addition products of alkylene oxide units, particularly ethylene oxide (EO) and/or propylene oxide (PO) units on alkylphenols, wherein the alkyl group of the alkylphenol contains between 6 and 18 carbon atoms, particularly preferably between 6 and 12 carbon atoms, principally 8, 9 or 10 carbon atoms and wherein preferably between 1 and 18 ethylene oxide (EO) units, particularly preferably between 5 and 15 EO units, principally 8, 9 or 10 EO units are added to the alkylphenol group, wherein the cited values are average values and wherein the alkyl group of the alkylphenol can be linear or methyl branched in the 2-position or can comprise linear and methyl branched groups in the mixture, as are typically present in oxoalcohol groups. In a particularly preferred embodiment, the non-ionic surfactant is an addition product of an average of 9 EO units on nonylphenol, wherein the alkyl group and the polyethylene group are preferably positioned meta to one another. A product of this type can be obtained, for example, under the name DISPONIL NP9 (Cognis, Germany).

In a further particularly preferred embodiment, the non-ionic surfactant is an addition product of ethylene oxide (EO) units on a fatty alcohol, wherein the fatty alcohol preferably contains between 10 and 22 carbon atoms, particularly preferably between 14 and 20 carbon atoms, principally between 16 and 18 carbon atoms and wherein preferably between 4 and 24 ethylene oxide (EO) units, particularly preferably between 10 and 22 EO units, principally 11, 12, 13, 19, 20 or 21 EO units are added to the fatty alcohol. Particularly preferred products that consist of a $C_{16-18}$-alcohol with 12 or 20 EO units are, for example, obtainable under the trade name EUMULGIN B1 or EUMULGIN B2 (Cognis, Germany).

In a further particularly preferred embodiment, the non-ionic surfactant is an addition product of ethylene oxide (EO) units on a fatty alcohol, wherein the fatty alcohol preferably contains between 8 and 22 carbon atoms, particularly preferably between 10 and 20 carbon atoms, principally between 12 and 18 carbon atoms and wherein preferably between 3 and 15 ethylene oxide (EO) units, particularly preferably between 5 and 11 EO units, principally 6, 7, 8, 9 or 10 EO units are added to the fatty alcohol. Particularly preferred products that consist of a $C_{12-18}$-alcohol with 7 or 9 EO units are, for example, obtainable under the trade name DEHYDOL LT7 and DEHYDOL 100 (Cognis, Germany).

In a further particularly preferred embodiment, the non-ionic surfactant is an addition product of ethylene oxide (EO) units on a fatty alcohol, wherein the fatty alcohol preferably contains between 18 and 26 carbon atoms, particularly preferably between 20 and 24 carbon atoms, principally 22 carbon atoms and wherein preferably between 6 and 16 ethylene oxide (EO) units, particularly preferably between 8 and 12 EO units, principally 9, 10 or 11 EO units are added to the fatty alcohol. A particularly preferred product that consists of a $C_{22}$-alcohol with 10 EO units is, for example, obtainable under the trade name MERGITAL B10 (Cognis, Germany).

In a further particularly preferred embodiment, the non-ionic surfactant is an addition product of ethylene oxide (EO) units and propylene oxide units on a fatty alcohol, wherein the fatty alcohol preferably contains between 6 and 18 carbon atoms, particularly preferably between 10 and 16 carbon atoms, principally between 10 and 12 or between 12 and 14 carbon atoms and wherein preferably between 1 and 10, particularly preferably between 3 and 7, principally 4, 5 or 6 EO units as well as preferably between 1 and 10, particularly preferably between 2 and 6, principally 3, 4, 5 or 6 PO units are added to the fatty alcohol. In a preferred embodiment, the non-ionic surfactant herein is a block copolymer, in which preferably the EO units are added to the fatty alcohol and the PO units follow on the EO units and wherein the alkyl group of the fatty alcohol can be linear or methyl-branched in the 2-position or may contain linear and methyl-branched radicals in the form of the mixtures typically present in oxoalcohol groups. A particularly preferred product that consists of a $C_{12}$-$C_{14}$-alcohol with 5 EO units and 4 PO units is, for example, obtainable under the name DEHYPPON LS 54 (Cognis, Germany). A further particularly preferred product that consists of a $C_{10-12}$-alcohol with 5 EO units and 5 PO units is, for example, obtainable under the name BIODAC 2/32 (Cognis, Germany).

In a further inventively preferred embodiment, the non-ionic surfactant is a fluorinated or fluorine-containing non-ionic surfactant. Here, particularly preferably it is an addition product of alkylene oxide units; particularly ethylene oxide (EO) units and/or propylene oxide units on an alkyl alcohol, wherein the alkyl alcohol preferably contains between 4 and 20 carbon atoms, particularly preferably between 6 and 18 carbon atoms, and wherein preferably between 1 and 18, particularly preferably between 2 and 16 EO units are added to the alkyl alcohol and wherein the compound, preferably the alkyl group, comprises at least one fluorine atom, preferably at least 5 fluorine atoms, especially between 5 and 30 fluorine atoms. In a particularly preferred embodiment, the compound or mixture of compounds is one with the formula $F(CF_2)_{1-7}CH_2CH_2O(CH_2CH_2O)_{1-15}H$. Such a non-ionic surfactant is obtainable for example under the name ZONYL FSO 100 (Dupont, France).

According to the invention, in a particular embodiment, the hydroxyl groups of the abovementioned non-ionic surfactants that carry hydroxyl groups can be partially or completely etherified or esterified. In this regard, there is especially an ether bond to a $C_{1-6}$ alkyl group, preferably to a methyl, ethyl iso-propyl or tert.-butyl group. Preferred ester bonds include those to a $C_{1-6}$ alkane carboxylic acid, especially to acetic acid or maleic acid.

In a preferred embodiment, the non-ionic surfactants are employed in carrier-bound form. In this regard, molecules particularly come into question as the carrier, which enable a covalent linkage and/or an intercalating linkage of the non-ionic surfactant. Macromolecular molecules with an acid function that enable the linkage of hydroxyl group-containing non-ionic surfactants in the form of ester bonds may be cited as the example of the first type of carriers. Cage molecules, which enable the uptake of non-ionic surfactants into the cage structure, may be cited as the example for the second type of carriers.

Preferred esters of non-ionic surfactants include the esters of silicic acids according to Formulas I and II. The silicic acid esters can be manufactured in particular by simple transesterification of silicic acid esters (n=1) or oligosilicic acid esters (n>1) of lower alcohols with the non-ionic surfactants. According to the reaction time and conditions, the lower alcohols are cleaved and the desired active substances are bonded, the alcohols along the Si—O—Si chain being more easily exchanged than the terminal alcohols.

Silicic acid esters according to one of the Formulas (I) or (II) and/or their mixtures are preferably employed.

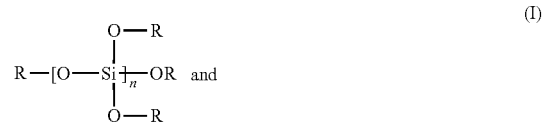

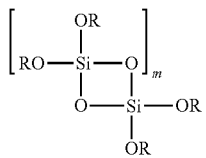
(II)

in which at least one R is a non-ionic surfactant and all other R groups, independently of each other, are selected from the group that comprises H, the aliphatic or aromatic, linear or branched, saturated or unsaturated, substituted or unsubstituted $C_{1-6}$-hydrocarbon groups, terpene alcohols, as well as polymers, and m has a value in the range 1 to 20 and n has a value in the range 1 to 100.

According to a further preferred embodiment, at least two or three R groups are a non-ionic surfactant.

The degrees of oligomerization "n" of the inventive silicic acid esters preferably lie between 1 and 20. In particularly preferred compounds n has a value between 1 and 15, particularly between 1 and 12 and principally between 1 and 10, in particular the values 4, 5, 6, 7 or 8.

The inventively used silicic acid esters are characterized by their good hydrolysis stability and can also be employed in aqueous media or in manufacturing processes for granulates, sealants, etc. without thereby suffering excessive loss in activity. Consequently, the release of the active substance from the inventive materials occurs slowly and in comparatively low amounts, such that there results a gradual release of the active substances from the product over a longer period of time.

According to a particularly preferred embodiment, one or a plurality of polymer groups can be found on the silicic acid esters. Preferably, those polymers that comprise free hydroxyl groups are employed to manufacture the silicic acid esters. In particular, the polymer group(s) are selected from starch and/or its derivatives, cellulose and/or its derivatives, polyvinyl alcohol, polyols, hydroxypolydimethylsiloxanes (quite particularly α,ω-dihydroxypolydimethylsiloxanes) and polyphenols, particularly polyvinyl alcohol. It is particularly preferred when a polymer group is found on the non-ionic surfactant-carrying silicic acid esters. A rather short-chain polymer is particularly preferred for use in sealants.

This specific embodiment has the advantage that the silicic acid esters can be individually tailored according to the field of application to the application objective or situation. For example, those polymers are particularly suitable for improving the processability of the materials, for increasing the adhesion, particularly to surfaces, and for influencing the release properties in the desired way.

Moreover, esters of the non-ionic surfactants with polymers can also be employed. These materials also yield better adaptability to the application objective, for example a better draw down or adhesion to surfaces or more favorable mixing conditions. Hydrolysis of the ester bond, e.g. on repeated contact with water, slowly releases the non-ionic surfactant, which can then develop its anti-adhesive action.

Such materials are particularly preferred from the reaction of the non-ionic surfactants with polymers that carry functional groups that are particularly selected from acid groups, acid chloride groups, ester groups, primary, secondary and tertiary amide groups.

According to the invention, polyacrylic acid, polyacrylic acid esters, polymethacrylic acid, polymethacrylic acid esters, polycarboxylic acids, (in particular carboxymethyl cellulose) as well as copolymers of the basic monomer (also with others than the cited monomers) and primary, secondary or tertiary polyacrylamides are preferably employed as the polymers. In particular, chain lengths from ca. 2000 to 300,000 g/mole are preferred in this context.

According to a further preferred embodiment, the polymer-ester is manufactured by reacting the active substance with monomers or polymers that carry one or more isocyanate groups. Urethanes, produced by the reaction of an alcohol function with an isocyanate group, also hydrolyze slowly and release the active substance in a controlled manner.

Preferably, monomeric aliphatic or aromatic mono-, di- or triisocyanates are employed. The urethanes or polyurethanes (by using isocyanates with a plurality of isocyanate groups) that result from the reaction can also hydrolyze and slowly release the active substances.

Preferred exemplary monoisocyanates are the linear or branched aliphatic monoisocyanates with 6 to 44 carbon atoms, for example hexyl isocyanate, heptyl isocyanate, octyl isocyanate, nonyl isocyanate, decyl isocyanate, undecyl isocyanate, dodecyl isocyanate, tridecyl isocyanate, quaterdecyl isocyanate, pentadecyl isocyanate, hexadecyl isocyanate, heptadecyl isocyanate, octadecyl isocyanate and the corresponding higher homologs of this series. Aromatic isocyanates such as phenyl isocyanate, benzyl isocyanate or biphenyl isocyanate are also preferred.

Preferred diisocyanates ($Q(NCO)_2$) are those in which Q is selected from an aliphatic, optionally substituted hydrocarbon group with 4 to about 15 carbon atoms, an aromatic, optionally substituted hydrocarbon group with 6 to about 15 carbon atoms, or an optionally substituted araliphatic hydrocarbon group with 7 to about 15 carbon atoms. Examples may be cited here: tetramethylene diisocyanate, hexamethylene diisocyanate, dodecamethylene diisocyanate, dimerfatty acid diisocyanate, 1,4-diisocyanato-cyclohexane, 1-isocyanato-3,3,5-trimethyl-5-isocyanato-methylcyclohexane (IDPI), 4,4'-diisocyanato-dicyclohexylmethyl, 4,4'-diisocyanatodicyclohexyl-2,2-propane, 1,3- and 1,4-diisocyanatobenzene, 2,4- or 2,6-diisocyanatotoluene or their mixtures, 2,2'-, 2, 4 or 4,4'-diisocyanato-diphenylmethane, tetramethylxylylene diisocyanate, p-xylylene diisocyanate as well as mixtures resulting from these compounds.

Toluene diisocyanate, hexamethylene diisocyanate and meta-tetramethylxylylene diisocyanate are particularly preferred.

Possible triisocyanates are primarily aromatic triisocyanates, such as for example thiophosphoric acid tris-(p-isocyanato-phenyl ester), the triphenylmethane-4,4',4"-triisocyanate as well as in particular the various isomers of the trifunctional homologs of diphenylmethane diisocyanate (MDI).

Furthermore, adducts of diisocyanates and low molecular weight triols, such as, for example trimethylol propane or glycerin, are also suitable as triisocyanates, particularly the adducts of aromatic diisocyanates and triols. Concerning these adducts, the abovementioned limitations are also valid with respect to the diisocyanate content as well as the content of polyisocyanates with a functionality >3.

Aliphatic triisocyanates, such as, for example the biuretization product of hexamethylene diisocyanate (HDI) or the isocyanated product of HDI or also the same trimerization products of isophorone diisocyanate (IPDI) are also suitable for the inventive compositions.

Polyisocyanates are the dimerization or trimerization products of the just cited preferred diisocyanates. Exemplary suitable isocyanates are the dimerization or trimerization products of the diisocyanate 2,4-toluene diisocyanate (2,4-TDI), 2,6-toluene diisocyanate (2,6-TDI), or a mixture of the cited isomers, 2,2'-diphenylmethane diisocyanate (2,2'-MDI), 2,4'-diphenylmethane diisocyanate (2,4'-MDI), 4,4'-diphenylmethane diisocyanate (4,4'-MDI), 1,5-naphthylene diisocyanate (NDI), 1,4-phenylene diisocyanate, 1,3-tetramethylxylylene diisocyanate (TMXDI), hydrogenated MDI (HMDI), isophorone diisocyanate (IPDI), hexamethylene-1,6-diisocyanate (HDI), 2-isocyanatopropylcyclohexyl isocyanate (IPCI), 2-butyl-2-ethyl-pentamethylene diisocyanate (BEPDI), lysine diisocyanate (LDI), 1,12-dodecyl diisocyanate, cyclohexyl-1,3- or -1,4-diisocyanate, 2-methylpentamethylene diisocyanate (MPDI) or the like, for example comprising urethane-, allophanate-, urea-, biuret-, uretidone-, carbodiimide- or ketone imine groups as obtained by dimerizing or trimerizing the abovementioned diisocyanates. Oligomeric or polymeric compounds carrying isocyanate groups, as accumulate, for example during the isocyanate manufacture or which remain as residual products in the distillation sump when distilling the crude isocyanate products, are particularly suitable. Examples of particularly suitable materials in this context are crude MDI, as obtained directly from the manufacture of MDI, and polymeric MDI as remains in the distillation sump after the distillation of MDI from the crude MDI.

It is preferred to add an appropriate amount of non-ionic surfactant to the monomers so as to produce the corresponding monomers. Thus, depending on the monomers used (monoisocyanates, diisocyanates or polyisocyanates), materials can be produced which carry one or a plurality, particularly one, two or three releasable active substances. It is also possible to produce a polymer chain having terminal active substance groups by means of a polymerization reaction.

For example, in sealants, such monomers or polymers can be added directly into the cartridge or added into a separate compartment as additives. Similarly, and also in the production of sealants, particularly those based on urethanes, the appropriate non-ionic surfactants can be added directly to the monomers of the sealants. The use of the reaction products of mono-, di- and/or triisocyanates with non-ionic surfactants or their derivatives in sealants is particularly preferred.

Exemplary polyhydroxy alcohols that can be added in the context of a polymerization reaction for the manufacture of the inventively usable materials as additional chain extenders are ethylene glycol, propylene glycol, 1,3-propanediol, 1,4-butanediol, 1,6-hexanediol, trimethylolpropane, glycerin, pentaerythritol, sorbitol, mannitol or glucose. Also, low molecular weight polyester diols like bis-(hydroxyethyl) esters of succinic acid, glutaric acid or adipic acid, or a mixture of two or more thereof, or low molecular weight diols containing ether groups, like diethylene glycol, triethylene glycol, tetraethylene glycol, dipropylene glycol, tripropylene glycol or tetrapropylene glycol can be used. Amines like ethylenediamine, hexamethylenediamine, piperazine, 2,5-dimethylpiperazine, 1-amino-3-aminomethyl-3,5,5-trimethylcyclohexane (isophoronediamine, IPDA), 4,4'-diamino-dicyclohexylmethane, 1,4-diaminocyclohexane, 1,2-diaminopropane, hydrazine, hydrazine hydrate, amino acid hydrazides like 2-aminoacetic acid hydrazide or bis-hydrazides like succinic acid bishydrazide are likewise suitable. In the context of an isocyanate polyaddition reaction, the co-use of small proportions of tri- or higher functional compounds is to obtain a certain degree of branching, just as it is possible to co-use the abovementioned tri- or higher functional polyisocyanates for the same purpose. Monohydroxy alcohols, such as n-butanol or n-dodecanol and stearyl alcohol can be co-used in small amounts.

In the context of the invention, cage molecules are understood in particular to include such organic macrocyclic molecules that possess a cage-like three-dimensional structure and which are able to enclose one or more "guest molecules" as "host molecules". Preferably, however, only one guest molecule is enclosed.

Accordingly, the controlled slow release of the non-ionic surfactants can occur by equilibrating a (often non-covalent) bond or by complexing the compound of a cage molecule.

The processability of the loaded cage molecule into the inventive products, particularly into those of hydrophobic character, is particularly good, due to the rather hydrophobic external shell of the cage substances.

A particularly major advantage of using cage molecules is that the substances that have diffused out of the products over time can be replaced by reloading the cage molecules. For this, concentrated solutions of the active substances are particularly suitable. With this in mind, products can likewise be manufactured, which do not initially comprise the free active substances, that is the non-ionic surfactants, complexed or bound into the cage molecules, but rather can be first loaded by these in the application circumstances. From the formulation point of view, this makes sense for applications known to the person skilled in the art.

Cucurbiturils, calixarenes, calixresorcarenes, cyclodextrins, cyclophanes, crown ethers, fullerenes, cryptophanes, carcerands, hemicarcerands, cyclotriveratrylenes, spherands and cryptands may be cited as organic cage molecules.

According to the invention, cucurbiturils, calixarenes and calixresorcarenes are particularly preferred, quite particularly cucurbiturils.

Cucurbiturils and their preparation are described in the literature, for example in U.S. Pat. Nos. 6,869,466; 6,793,839; 6,639,069; and 6,365,734 (each of which is incorporated herein by reference in its entirety) together with additional references cited therein. In the context of the invention, a usable cucurbituril is basically understood to mean every material, which has been described in the literature as belonging to this class of compound. Included in this definition are cucurbiturils and substituted cucurbiturils described in WO 00/68232 as well as the cucurbituril derivatives described in EP-A 1 094 065. Instead of a single cucurbituril, substituted cucurbiturils or cucurbituril derivatives, likewise mixtures of two or more of this type of compounds can be used. In the following text, when reference is made to a cucurbituril, and when anything else is not expressly mentioned, then in the same way it is understood to mean a chemically pure cucurbituril or also a mixture of two or more cucurbiturils, substituted cucurbiturils and/or cucurbituril derivatives. Accordingly, the cited quantities of cucurbiturils, when otherwise not expressly mentioned, always refer to the total quantity of one or the plurality of cucurbiturils, substituted cucurbiturils and/or cucurbituril derivatives.

In the scope of the present invention, cucurbit[n]urils with a ring size 5 to 11, as well as their mixtures are preferred, wherein cucurbit[6]uril as well as their mixtures with a predominant cucurbit[6]uril content are particularly preferred.

Moreover, calix[n]arenes according to Formula (VIII) can be employed.

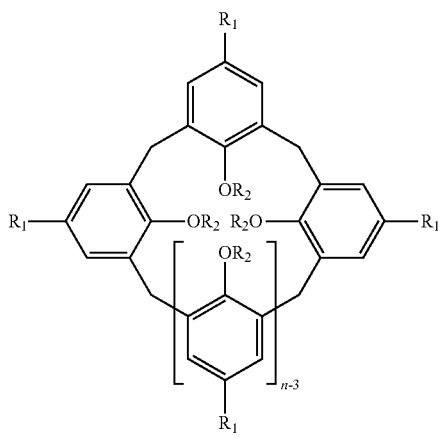

(VIII)

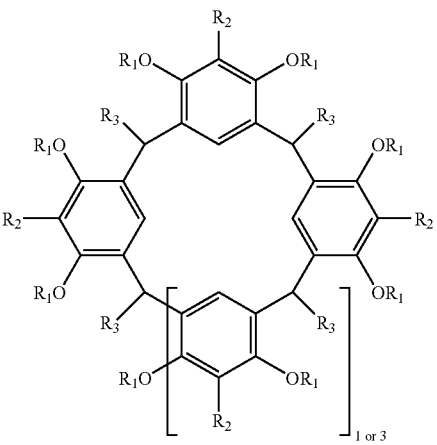

(IX)

wherein:

$R^1$ is selected from $R^1$=H, alkyl, aryl, alkenyl, alkynyl as well as substituted alkyls, aryls, alkenyls, alkynyl substituted by groups selected from: —OH, —OR', —NH$_2$, —NHR', —NR'R", —NR'R" R'''$^+$, NO$_2$, halogen, SO$_3$H, SO$_3$M (M=alkali metal, earth alkali metal), carboxylic acids, ketones, aldehydes, amides, esters, —SO$_2$NH$_2$, SO$_2$NHR, SO$_2$NR'R", —SO$_2$ halogen, sulfur-, phosphorus-silicon-containing groups;

and $R_2$ is selected from $R_2$=H, alkyl, aryl, alkenyl, alkynyl as well as substituted alkyls, aryls, alkenyls, alkynyl substituted by groups selected from: —OH, —OR', —NH$_2$, —NHR', —NR'R", —NR'R" R'''$^+$, —NO$_2$, halogen, —SO$_3$H, —SO$_3$M (M=alkali metal, earth alkali metal), carboxylic acids, ketones, aldehydes, amides, esters, —SO$_2$NH$_2$, SO$_2$NHR, SO$_2$NR'R''', —SO$_2$ halogen, sulfur-, phosphorus- or silicon-containing groups;

wherein R', R", R''' independently of one another are selected from H, alkyl, aryl, alkenyl, alkynyl, substituted alkyls, aryls, alkenyls, and alkynyl.

Here, calixarenes are preferred according to Formula (VIII) in which:

$R^1$ is selected from $R_1$=H, alkyl, aryl, alkenyl, alkynyl as well as substituted alkyls, aryls, alkenyls, alkynyl substituted by groups selected from: —OH, —OR', —NH$_2$, —NHR', —NR'R", —NR'R" R'''$^+$, NO$_2$, halogen, SO$_3$H, carboxylic acids, ketones, aldehydes, amides, esters, —SO$_2$NH$_2$; and $R_2$ is selected from $R_2$=H, alkyl, aryl, alkenyl, alkynyl as well as substituted alkyls, aryls, alkenyls, alkynyl substituted by groups selected from: —OH, —OR', —NH$_2$, —NHR', —NR'R", —NR'R"R'''$^+$, —NO$_2$, halogen, —SO$_3$H, carboxylic acids, ketones, aldehydes, amides, esters, —SO$_2$NH$_2$;

wherein R', R", R''' independently of one another are selected from H, alkyl, aryl, alkenyl, alkynyl, substituted alkylenes, arylenes, alkenylenes, alkynylenes.

In the context of the present invention, calix[n]arenes of ring size n=4 to 12, together with their mixtures, are preferred, wherein calix[6]arene and/or calix[4]arene as well as their mixtures with a predominant calix[6]arene and/or calix[4]arene content are particularly preferred.

Furthermore, calix[n]resorcarenes, also known as resorcinarenes according to Formula (IX) may be used, where n reflects the number of chain members and may be 4 or 6.

wherein $R_1$, $R_2$ and $R_3$ are selected from:

$R_1$ is selected from $R_1$=H, alkyl, aryl, alkenyl, alkynyl as well as substituted alkyls, aryls, alkenyls, or alkynyl substituted by groups selected from: —OH, —OR', —NH$_2$, —NHR', —NR'R", —NR'R"R'''$^+$, NO$_2$, halogen, SO$_3$H, SO$_3$M (M=alkali metal, alkali earth metal), carboxylic acids, ketones, aldehydes, amides, esters, —SO$_2$NH$_2$, SO$_2$NHR, SO$_2$NR$_2$, —SO$_2$ halogen, sulfur-, phosphorus-silicon-containing groups;

and $R_2$, $R_3$ independently of one another are selected from $R_2$, $R_3$=H, alkyl, aryl, alkenyl, alkynyl as well as substituted alkyls, aryls, alkenyls, alkynyl substituted by groups selected from: —OH, —OR', —NH$_2$, —NHR', —NR'R", —NR'R"R'''$^+$, NO$_2$, halogen, SO$_3$H, SO$_3$M (M=alkali metal, alkali earth metal), carboxylic acids, ketones, aldehydes, amides, esters, —SO$_2$NH$_2$, SO$_2$NHR, SO$_2$NR$_2$, —SO$_2$ halogen, sulfur-, phosphorus-, silicon-containing groups;

and wherein R', R", R''' independently of one another are selected from H, alkyl, aryl, alkenyl, alkynyl, as well as substituted alkylenes, arylenes, alkenylenes, alkynylenes.

Here, calix[4]resorcarenes and/or calix[6]resorcarenes are preferred according to Formula (IX) in which:

$R_1$ is selected from $R_1$=H, alkyl, aryl, alkenyl, alkynyl as well as substituted alkylenes, arylenes, alkenylenes, alkynylenes substituted by groups selected from: —OH, —OR', —NH$_2$, —NHR', —NR'R", —NR'R"R'''$^+$, NO$_2$, halogen, SO$_3$H, carboxylic acids, ketones, aldehydes, amides, esters, —SO$_2$NR'R";

and $R_2$, $R_3$ independently of one another are selected from $R_2$, $R_3$=H, alkyl, aryl, alkenyl, alkynyl as well as substituted alkylenes, arylenes, alkenylenes, alkynylenes substituted by groups selected from: —OH, —OR', —NH$_2$, —NHR', —NR'R", —NR'R"R'''$^+$, NO$_2$, halogen, SO$_3$H, carboxylic acids, ketones, aldehydes, amides, esters, —SO$_2$NR'R";

wherein R', R", R''' independently of one another are selected from H, alkyl, aryl, alkenyl, alkynyl, as well as substituted alkylenes, arylenes, alkenylenes, alkynylenes.

It is particularly preferred when $R_2$=$R_3$, i.e., $R_2$ and $R_3$ represent the same substituents.

According to the invention, the non-ionic surfactants and/or their carrier-bound forms are preferably added in quantities of up to 20 wt. %, particularly preferably in quantities between 0.001 and 3 wt. % and particularly in quantities between 0.01 and 1.5 wt. %.

The quantities that provide the desired result in the final product can be significantly less than mentioned, as for many products, dilution has to be taken into account. For detergents, for example, a dilution factor (ratio of detergent concentrate: water) has to be calculated from 1:20 to 1:200. The dilution ratio for detergents is often between 1:60 and 1:100, for example 1:80.

Microorganisms

In a preferred embodiment, microorganisms are understood to mean bacteria and fungi. Particularly preferred fungi are here yeasts, molds, dermatophytes and keratinophilic fungi.

According to a particularly preferred embodiment, the adhesion of bacteria is reduced by the use of non-ionic surfactants, in particular the adhesion of gram-negative and gram-positive bacteria, principally the adhesion of pathogenic bacteria selected from *Propionibacterium acnes, Stapylococcus aureus, Streptococcus* of group A (beta-hemolytic S.), *S. pyogenes, Corynebacterium* spp. (particularly *C. tenuis, C. diphtheriae, C. minutissimum*), *Micrococcus* spp. (particularly M. sedentarius), *Bacillus anthracis, Neisseria meningitidis, N. gonorrhoeae, Pseudomonas aeruginosa, P. pseudomallei, Borrelia burgdorferi, Treponema pallidum, Mycobacterium tuberculosis, Mycobacterium* spp., *Escherichia coli* as well as *Streptococcus* spec. (particularly *S. gordonii, S. mutans*), *Actinomyces* spec. (particularly *A. naeslundii*), *Salmonella* spec., Actinobacteria (particularly *Brachybacterium* spec.), alpha-Proteobacteria (particularly *Agrobacterium* spec.), beta-Proteobacteria (particularly *Nitrosomonas* spec.), *Aquabacterium* spec., Hydrogenophaga, gamma-Proteobacteria, *Stenotrophomonas* spec.,*Xanthomonas* spec. (campestris),*Neisseria* spec.,*Haemophilus* spec. as well as all microorganisms that are described by Paster et al. (J. Bac. 183 (2001) 12, 3770-3783).

In the context of the invention, yeasts are monocellular fungi that predominantly reproduce by budding. Yeast fungi do not represent an independent taxonomical category in the system of the fungi. The majority of yeasts are systematically categorized in the Endomycetes. However, beside this, with various other fungi, budding cell stages, known as yeast stages, also appear in the development cycle or under specific environmental conditions. Such monocellular, yeast-like, budding growth forms appear with the ascomycetes, but also with the zygomycetes, basidomycetes and deuteromycetes. According to the invention, all these growth forms are to be understood as yeasts.

According to a further particular embodiment, the use of non-ionic surfactants reduces the adhesion of human pathogenetic fungi. That includes, for example, the human pathogenic species of fungi from the classes ascomycota, basidomycota, deuteromycota and zygomycota, particularly human pathogenic forms of candida.

The human pathogens of the candida species populate skin and mucous membranes even for healthy persons. With stronger reproduction of the fungal cells, e.g., after damage of the bacterial mucous membrane flora by anti-biotics, they cause local inflammations that are also named candidiasis. They appear particularly in the buccal and genital areas (oral and vaginal candidiasis). Skin and diaper candidiasis are also known. The mucous membrane is reddened, lesions are found and a white coating and itching develop.

According to the invention, in particular the adhesion of fungi of the *Candida* species (abbreviated to C. in the following) is reduced, selected from *C. aaseri, C. actiscondensi, C. acutus, C. agrestis, C. albicans, C. amapae, C. anatomiae, C. ancudensis, C. antarctica, C. antillancae, C. apicola, C. apis, C. aquaetextoris, C. aquatica, C. atlantica, C. atmosphaerica, C. auringiensis, C. azyma, C. beechii, C. ben-hamii, C. bertae, C. berthetii, C. blankii, C. boidinii, C. boleticola, C. bombi, C. bondarzewiae, C. brumptii, C. buffonii, C. buinensis, C. cacaoi, C. cantarellii, C. capsuligena, C. cariosilignicola, C. caseinolytica, C. castellii, C. catenulata, C. chalmersi, C. chilensis, C. chiropterorum, C. ciferii, C. claussenii, C. coipomensis, C. colliculosa, C. conglobata, C. curiosa, C. cylindracea, C. dendrica, C. dendronema, C. deserticola, C. diddensiae, C. diffluens, C. diversa, C. drymisii, C. dubliniensis, C. edax, C. entomophila, C. eremophila, C. ergatensis, C. ernobii, C. etchellsii, C. etchellsii, C. ethanolica, C. ethanothermophilum, C. evantina, C. fabianii, C. famata, C. fennica, C. flareri, C. fluviotilis, C. fragariorum, C. fragi, C. fragicola, C. freyschussii, C. friedrichii, C. fructus, C. fusiformata, C. geochares, C. glabrata, C. glaebosa, C. graminis, C. gropengiesseri, C. guilliermondii, C. haemulonii, C. hellenica, C. heveanensis, C. holmii, C. homilentoma, C. humicola, C. humilis, C. iberica, C. incommunis, C. inconspicua, C. ingens, C. insectalens, C. insectamans, C. insectorum, C. intermedia, C ishiwadae, C. japonica, C. javanica, C. karawaiewii, C. kefyr, C. kruisii, C. krusei, C. krusoides, C. lactiscondensi, C. lambica, C. laureliae, C. lipolytica, C llanquihuensis, C. lodderae, C. Iusitaniae, C. magnoliae, C. malicola, C. maltosa, C. maris, C. maritima, C. melibiosica, C. melinii, C. membranaefaciens, C. mesenterica, C. methanosorbosa, C milleri, C. mogii, C. molischiana, C. monosa, C. montana, C. mucilaginosa, C. multisgemmis, C. musae, C. muscorum, C. mycoderma, C. naeodendra, C. nakasei, C. nemodendra, C. nitratophila, C. norvegensis, C novakii, C. oleophila, C. oregonensis, C. palmyrana, C. paludigena, C. parapsilosis, C. pararugosa, C. pelliculosa, C. peltata, C. periphelosum, C. petrohuensis, C. pignaliae, C. pintolopesii, C. pinus, C. placentae, C. polymorpha, C. populi, C. pseudotropicalis, C. psychrophila, C. pulcherrima, C. punica, C. quercitrusa, C. quercuum, C. railenensis, C. ralunensis, C. reukaufii, C. rhagii, C. rugopelliculosa, C. rugosa, C. saitoana, C. sake, C. salmanticensis, C. santamariae, C. santjacobensis, C. savonica, C. schatavii, C. sequanensis, C. shehatae, C. silvae, C. silvanorum, C. silvicultrix, C. solani, C. sonorensis, C. sophiae-reginae, C. sorboxylosa, C. spandovensis, C. sphaerica, C. stellata, C. stellatoidea, C. succiphila, C. sydowiorum, C. tanzawaensis, C. tenuis, C. tepae, C. terebra, C. torresii, C. tropicalis, C. tsuchiyae, C. tsukubaensis, C. utilis, C. valdiviana, C. valida, C. vanderwaltii, C. vartiovaarai, C. versatilis, C. vini, C. viswanathii, C. wickerhamii, C. xestobii, C. zeylanoides.*

According to a further preferred embodiment, the adhesion of fungi of the species *Rhodotorula* spp., *Cryptococcus* spp., *Exophilia* spp., *Hormoconis* spp. is reduced.

According to the invention, the adhesion of the medically relevant forms of *Candida* are particularly preferably reduced, for example *C. albicans, C. boidinii, C. catenulata, C. ciferii, C. dubliniensis, C. glabrata, C. guilliermondii, C. haemulonii, C. kefyr, C. krusei, C. lipolytica, C. lusitaniae, C. norvegensis, C. parapsilosis, C. pulcherrima, C. rugosa, C. tropicalis, C. utilis, C. viswanathii.* Particularly preferred are *C. albicans, C. stellatoidea, C. tropicalis, C. glabrata* and *C. parapsilosis.* The mycel form of *Candida* is considered as the human pathogenic form of the fungus. The reduction in adhesion of *Candida* to textiles or plastics, for example, reduces the risk of re-infection, without increasing the development of resistance.

According to the present invention, molds are understood to mean those fungi which have their habitat in the soil, on foods and/or animal feed or in concentrated nutritional solutions, which form mycels, and which obtain their nutrients from organic substances that are thereby decomposed (saprobiontic or saprophytic mode of life). Moreover, they reproduce predominantly asexually by means of spores (in particular sporangiospores or by conidium) and form, if ever, only very small sexual reproductive organs.

That includes, for example, species from the classes Ascomycota, Basidiomycota, Deuteromycota and Zygomycota, in particular all species from the genera *Aspergillus, Penicillium, Cladosporium* and *Mucor* as well as *Stachybotrys, Phoma, Alternaria, Aureobasidium, Ulocladium, Epicoccum, Stemphyllium, Paecilomyces, Trichoderma, Scopulariopsis, Wallemia, Botrytis, Verticillium* and Chaetonium.

The Ascomycota include all species of the genera *Aspergillus, Penicillium* and *Cladosporium*. These fungi develop spores that on contact with the skin or the respiratory tracts have a strong potential for causing allergies. The Basidomycota include, for example, *Cryptococcus neoformans*. The Deuteromycota include all the known genera of mold, particularly those that because of the lack of a sexual phase are not classified in the classes Ascomycota, Basidiomycota or Zygomycota.

Non-ionic surfactants are particularly preferably suitable for reducing the adhesion of all species of the genus *Aspergillus* to surfaces, quite particularly preferably the species selected from *Aspergillus aculeatus, Aspergillus albus, Aspergillus alliaceus, Aspergillus asperescens, Aspergillus awamori, Aspergillus candidus, Aspergillus carbonarius, Aspergillus carneus, Aspergillus chevalieri, Aspergillus chevalieri* var. *intermedius, Aspergillus clavatus, Aspergillus ficuum, Aspergillus flavipes, Aspergillus flavus, Aspergillus foetidus, Aspergillus fumigatus, Aspergillus giganteus, Aspergillus humicola, Aspergillus intermedius, Aspergillus japonicus, Aspergillus nidulans, Aspergillus niger, Aspergillus niveus, Aspergillus ochraceus, Aspergillus oryzae, Aspergillus ostianus, Aspergillus parasiticus, Aspergillus parasiticus* var. *globosus, Aspergillus penicillioides, Aspergillus phoenicis, Aspergillus rugulosus, Aspergillus sclerotiorum, Aspergillus sojae* var. *gymnosardae, Aspergillus sydowi, Aspergillus tamarii, Aspergillus terreus, Aspergillus terricola, Aspergillus toxicarius, Aspergillus unguis, Aspergillus ustus, Aspergillus versicolor, Aspergillus vitricolae* and *Aspergillus wentii*. Particularly preferably, the adhesion of *Aspergillus flavus* and *Apsergillus nidulans* is reduced or essentially prevented.

Keratinophilic fungi are understood to mean those skin and/or hair fungi that grow in calloused skin and their adnexa (particularly hair and/or nails). They are particularly understood to mean Dermatophytes and all species of the genus *Malassezia*. According to the invention, Dermatophytes are understood to mean all species of the genera *Trichophyton, Microsporum* and *Epidermophyton.*

The keratinophilic fungus Malassezia, a yeast fungus, is responsible for increased dandruff formation of the skin, for example on the head (hair dandruff). Furthermore, this organism is considered to be responsible for the skin disease pityriasis versicolor. In particular, it is therefore an advantage to reduce or essentially prevent the adhesion of *Malassezia*, particularly those of the species *M. furfur* (also known under the name *Pityrosporum ovale*), *M. pachydermatis, M. sympodialis* and/or *M. Globosa.*

According to a preferred embodiment, the keratinophilic fungi are selected from *Trichophyton mentagrophytes, T. rubrum, T. asteroides, T. concentrium, T. equinum, T. meginii, T. gallinae, T. tonsurans, T. schoenleinii, T. terrestre, T. verrucosum, T. violaceum, Microsporum canis, Microsporum audounii, M. gypseum, Epidermophyton flossocum, Malassezia furfur, M. sympodialis, M. globosa* and *M. pachydermatis.*

According to a further preferred embodiment, the use of non-ionic surfactants reduces the adhesion of dermatophytes to surfaces. In particular, the Dermatophytes are selected from *Trichophyton mentagrophytes, T. rubrum, T. asteroides, T. concentrium, T. equinum, T. meginii, T. gallinae, T. tonsurans, T. schoenleinii, T. terrestre, T. verrucosum, T. violaceum, Microsporum canis, Microsporum audounii, M. gypseum* and *Epidermophyton* flossocum.

According to a further embodiment, the use of non-ionic surfactants reduces the adhesion of algae, of human, animal and/or vegetal pathogenic viruses as well as of bacteriophages.

Algae are mono- to pluricellular, differently colored, primary photoautotrophic plants or photoautotrophic bacteria mostly from thallophytic organization, whose gametes and spore building organs are generally monocellular and possibly possess hulls of sterile cells. Algae are differentiated according to their pigmentation into green, red, blue and brown algae, the green and blue algae being principally relevant to cladding and building materials. The relevant members of the blue algae (cyanobacteria) are of the genera *Anabaena, Anacystis*, e.g. *Anacystis montana, Gloeocapsa, Lyngbia, Nostoc, Oscillatoria*, e.g. *Oscillatoria lutea, Phormidium, Schiszothrix* and *Scytonema*. Genera of the green algae (chlorophyta) are for example *Chlorella, Choricystis, Chlamydomonas, Chlorococcum, Stichcoccus*, particularly *Stichcoccus bacillaris, Ulothrix* and *Trentepholia*, particularly *Trentepholia odorata*. According to the invention, the adhesion of algae to surfaces can now be reduced by the use of non-ionic surfactants, particularly in very moist areas as well as aquariums, but also to such surfaces that are subject to weathering, such as, e.g., building materials, including in particular sealants or extruded sealing.

Preferred Articles

Preferred articles of the present invention are textiles, furs, paper, hides, leather and packaging, particularly those for foodstuffs, particularly preferred articles are filter media, building materials and building auxiliaries, which comprise non-ionic surfactants, particularly fluorinated non-ionic surfactants in order to reduce the adhesion of microorganisms to surfaces, and which are treated with and/or coated with them, wherein the non-ionic surfactants are preferably not covalently bonded to the materials.

Treatment of the packaging, surfaces, textiles, furs, paper, hides or leather is carried out by methods known to the person skilled in the art, for example by dipping in a suitable concentrated solution of an inventive agent or by spraying with such a solution. Thus, for example, works of art on paper, vellum, wood and/or canvas can be protected or rid of infestation from microorganisms, particularly mold infestation. The treatment of the filter media, building materials or building auxiliaries is carried out, for example, by applying, particularly preferably, however, by mechanical incorporation of the non-ionic surfactants or of a suitably concentrated solution of the non-ionic surfactants on or into the filter media, building materials or building auxiliaries. Thus the non-ionic surfactants can be mixed mechanically, e.g., by stirring, in the materials in question before their use or alternatively, they can also be already incorporated in them during the manufacture of the materials.

Preferably, the inventively treated building materials or building auxiliaries are selected from adhesive compounds, sealants, fillers and coating compounds, plastics, varnishes, paints, plaster, mortar, screeds, concrete, insulation materials and undercoats. Particularly preferred building materials or building auxiliaries are joint sealants (e.g., silicone-containing joint sealants), wallpaper paste, plaster, carpet fixers, silicone adhesives, and tile adhesives.

Sealants and particularly joint sealants typically comprise organic polymers and in certain cases mineral or organic fillers and other additives.

Suitable polymers are for example thermoplastic elastomers as described in DE 3602526, preferably polyurethanes and acrylates. Suitable polymers are also mentioned in U.S. Pat. No. 4,910,242, U.S. Pat. No. 5,525,654 and DE 4009095 as well as in U.S. Pat. No. 6,184,274 and U.S. Pat. No. 5,412,015, which are incorporated herein by reference in their entirety.

The inventive sealants (sealants or sealant mixtures) preferably comprise 0.001-3.0 wt. % non-ionic surfactant. Amounts between 0.01 and 1.0 wt. % are particularly preferred.

According to the invention, the treatment of the inventive sealants can occur in the uncured or cured state below 60° C. In the context of the invention, sealants are materials according to DIN EN 26927, in particular those that cure plastically or elastically as the sealants. The inventive sealants can comprise all the typical additives that are appropriate for sealants, such as, for example typical thickeners, reinforcing fillers, crosslinkers, crosslinking catalysts, pigments, coupling agents or other volume extenders. The deposition or incorporation of the non-ionic surfactants can be carried out by dispersion techniques known to the person skilled in the art, e.g., by the use of dispersion equipment, kneaders, planetary mixers etc., in the absence of moisture and oxygen, into both the finished sealants as well as constituents of the sealants or together with one or a plurality of components of the sealant.

Even the treatment of already cured, crosslinked sealant surfaces can be carried out by depositing solutions or suspensions of the inventively used substance, as the active substance is transported into the sealant by swelling or diffusion.

Inventively usable sealants can be manufactured both from silicones, urethanes as well as acrylics or for example based on MS-polymers. Urethane-based sealants have been disclosed, for example, in Ullmann's Encyclopedia of Industrial Chemistry (8th edition 2003, chapter 4) and U.S. Pat. No. 4,417,042. Silicone sealants are known to the person skilled in the art, for example, from EP 0 118 030 A, EP 0 316 591 A, EP 0 327 847 A, EP 0 553 143 A, DE 195 49 425 A and U.S. Pat. No. 4,417,042. Examples of acrylic sealants have been disclosed, inter alia, in WO 01/09249 or U.S. Pat. No. 5,077,360. Examples of sealants based on MS-polymers have been disclosed, for example, in EP 0 824 574, U.S. Pat. No. 3,971,751, U.S. Pat. No. 4,960,844, U.S. Pat. No. 3,979,344, U.S. Pat. No. 3,632,557, DE 4029504, EP 601 021 or EP 370 464.

In a particularly preferred embodiment, the joint sealing compound concerns a silicone-based joint sealing compound, particularly from acetato-, alkoxy-, oximo-, benzamido- and aminosilicones. The joint sealing compound here preferably comprises polyorganosiloxanes and organosilicone compounds having hydrolyzable groups as are described and in the amounts mentioned in the U.S. Pat. No. 5,378,406, the disclosure of which is incorporated herein by reference in its entirety.

In particular, room temperature crosslinkable systems, as described, for example in EP 0 327 847 or U.S. Pat. No. 5,077,360, are preferred. They can concern multicomponent systems, wherein the catalyst and the crosslinker can be separated in the multicomponent system (for example disclosed in the U.S. Pat. No. 4,891,400 and U.S. Pat. No. 5,502,144), or other silicone RTV 2K-systems, in particular platinum-free systems.

One-component systems are particularly preferred and comprise all the components to form a sealant, and are stored under the exclusion of air humidity and/or oxygen from the air; at the point of use, they cure by reaction with the oxygen from the air and/or the air humidity. Particularly preferred are the silicone-neutral systems, in which the reaction of crosslinkers with the water of the surrounding air does not afford corrosive, acidic, basic or odor intensive cleavage products. Examples of such systems are disclosed in DE 195 49 425, U.S. Pat. No. 4,417,042 or EP 0 327 847.

The sealants and in particular the joint sealing compounds can comprise aqueous or organic solvents. The organic solvents can include hydrocarbons like cyclohexane, toluene or also xylene or petrol ether. Additional solvents are ketones like methyl butyl ketone or chlorinated hydrocarbons.

The sealants can further comprise additional rubbery polymers. These include relatively low-molecular weight, commercial types of polyisobutylene, polyisoprene or also polybutadiene-styrene. The co-use of degraded natural rubber or neoprene rubber is also possible. Here, room temperature flowable types, which are often called "liquid rubber", can also be used.

The inventive sealants can be used to bond or joint the most varied materials together. Here, the use is mainly considered on concrete, on glass, on plaster and/or enamel as well as ceramic and porcelain. However, the jointing or sealing of molded parts or profiles of aluminum, steel, zinc or also of plastics like PVC or polyurethanes or acrylic resins is also possible. Finally, the sealing of wood or wooden materials to the most different other materials is noted.

The stability of joint sealants is generally realized by the addition of finely dispersed solids, also known as fillers. These can be differentiated into organic and inorganic types. Silicic acid/silicon dioxide (coated or uncoated), chalk (coated or uncoated) and/or zeolites are preferred inorganic fillers. In addition, the zeolites can also function as drying agents. Exemplary organic fillers include PVC powder. In general, fillers make a significant contribution to the required internal strength of the sealant after application, such that the sealant is prevented from running out of or receding from any vertical joints. The mentioned additives and fillers can be subdivided into pigments and thixotropicizing fillers also designated by the abbreviation thixotropic agents.

Known thixotropic agents like bentonites, kaolins or also organic compounds like hydrogenated castor oil or its derivatives with multifunctional amines or the reaction products of stearic acid or ricinoleic acid with ethylenediamine are suitable thixotropic agents. The co-use of silicic acid, particularly pyrolyzed silicic acid, has proven to be particularly beneficial. Furthermore, swellable polymer powders are basically considered as thixotropic agents. Examples of these are polyacrylonitrile, polyurethane, polyvinyl chloride, polyacrylates, polyvinyl alcohols, and polyvinyl acetates as well as the corresponding copolymers. Particularly good results are obtained with finely dispersed polyvinyl chloride powder. Besides the thixotropic agents, in addition, adhesion promoters such as mercaptoalkylsilane can also be employed. It has proven convenient to employ a monomercaptoalkyltrialkoxysilane. Mercaptopropyltrimethoxysilane, for example, is commercially available.

The properties of a joint sealing compound can be further improved if additional components are added to the plastic powder used as the thixotropic agent. Here, this concerns materials that fall in the category of plasticizers or swelling agents and swelling auxiliaries used in plastics.

Plasticizers, for example, from the class of the phthalic acid esters, can be considered particularly for joint sealing compounds based on urethanes or acrylics. Examples of applicable compounds from this class of substances are dioctyl phthalate, dibutyl phthalate and benzyl butyl phthalate. Further suitable classes of substances are chloroparaffins, alkylsulfonates for example phenols or cresols as well as fatty acid esters.

For silicone sealants, suitable plasticizers are silicone oils, particularly preferably polydimethylsiloxanes, as well as hydrocarbons and/or their mixtures, of which hydrocarbons in particular or their mixtures with a boiling point above 200° C., particularly above 230° C.

Those low molecular weight organic substances that are miscible with the polymer powder and the plasticizer can be used as the swelling auxiliaries. These types of swelling auxiliaries can be found in the relevant plastics and polymer handbooks intended for the person skilled in the art. Preferred swelling auxiliaries for polyvinyl chloride powder are esters, ketones, aliphatic hydrocarbons, and aromatic hydrocarbons, as well as alkyl substituted, aromatic hydrocarbons.

The known substances titanium dioxide, iron oxides and carbon black are used as the pigments and colorants in these applications.

The storage stability is improved by adding known stabilizers like benzoyl chloride, acetyl chloride, methyl toluenesulfonate, carbodiimides and/or polycarbodiimides to the sealants. Olefins having 8 to 20 carbon atoms have proven to be particularly good stabilizers. In addition to their stabilizing action, they can also fulfill the tasks of plasticizers or swelling agents. Olefins having 8 to 18 carbon atoms, particularly when the double bond is in the 1,2 position, are preferred. The best results are obtained when the molecular structure of these stabilizers is linear.

By the inventive use of non-ionic surfactants to reduce the adhesion of microorganisms, in particular molds, to surfaces, the problem of resistance development due to biocides is circumvented. By the reduction of adhesion of molds to the surfaces, a plurality of desired effects is achieved for the application in building materials and building auxiliaries susceptible to mold, in particular sealants and joint sealants: discoloration from pigmented molds is prevented, the dissemination of the mold infestation is slowed down and the allergic exposure is reduced.

A further preferred embodiment of the present invention includes wallpaper adhesives comprising preferably 0.000001 to 3 wt. % non-ionic surfactants. The wallpaper adhesives concern wallpaper pastes of aqueous solutions of hydrocolloids like methyl cellulose, methyl hydroxypropyl cellulose or water-soluble starch derivatives or for example aqueous dispersions of film-forming high molecular weight materials like polyvinyl acetate, particularly in combination with the already cited cellulosic and starch derivatives.

The filter media employed can be all known types, as long as they are suitable for use in water filtration or air filtration units, particularly for air-conditioning units or air humidifiers. In particular, filter materials of cellulose, glass fibers, PVC-fibers, polyester fibers, polyamide fibers, particularly nylon fibers, non-wovens, sintered materials and membrane filters are to be mentioned.

Depending on the conditions of use of the agents, the concentration of added non-ionic surfactants in the inventive agents used to reduce the adhesion of microorganisms to surfaces can be varied over a wide scale by the person skilled in the art.

The inventive agents are manufactured according to conventional formulations known to the person skilled in the art. The non-ionic surfactants can be added both to the already prepared finished agents but also during the manufacturing process.

Detergents and Cleansing Agents.

For detergents, it was already described that non-ionic surfactants can be employed here for cleaning the washing. However, an anti-adhesive affect has not been described up to now.

Accordingly, a further subject matter of the invention is the use of non-ionic surfactants in detergents and/or cleansing agents to reduce the adhesion of microorganisms to articles treated with these detergents and/or cleansing agents.

Such detergents and cleansing agents can comprise relatively low amounts of substances without polluting the wastewater. As they are used in concentrated form and are diluted to the corresponding active concentrations in the wash liquor, the active substances have to be used in a correspondingly higher concentration. The detergents and cleansing agents are normally diluted with water in the ratio 1:40 to 1:200.

According to the invention, non-ionic surfactants can also be added to cleansing agents for cleaning hard surfaces, such as for example floors, tiles, wall tiles, plastics as well as other hard surfaces in the household, in public sanitary facilities, in swimming baths, saunas, sports facilities or in medical or massage practices.

Besides the pathogenic microorganisms (particularly fungi and bacteria), particularly *Pseudomonas aeruginosa, Salmonelle* spec., *Actinobacteria* (particularly *Brachybacterium* spec.), alpha-Proteobacteria (particularly *Agrobacterium* spec.), beta-Proteobacteria (particularly *Nitrosomonas* spec., *Aquabacterium* spec., Hydrogenophaga), gamma-Proteobacteria (particularly *Stenotrophomonas* spec., *Xanthomonas* spec (campestris)) are found on such surfaces.

In the broadest sense of the scope of the invention, detergents and cleansing agents are understood to mean surfactant-containing preparations in solid form (particles, powder etc.), semi-solid form (pastes etc.), liquid form (solutions, emulsions, suspensions, gels etc.) and gaseous-like form (aerosols etc.) that in regard to an advantageous action in use can also comprise additional surfactants beside the fluorinated non-ionic surfactants, normally beside additional components that are usual for each of the end uses. Examples of such surfactant-containing preparations are surfactant-containing detergent preparations, surfactant-containing cleansing agents for hard surfaces, or surfactant-containing freshening preparations, each of which can be solid or liquid, however, they can also be in a form that includes solid and liquid components or partial amounts of the components alongside one another.

The detergents and cleansing agents comprise typically comprised ingredients, like anionic, non-ionic, cationic and amphoteric surfactants, inorganic and organic builders, special polymers (for example those with cobuilder properties), foam inhibitors, colorants and optional fragrances (perfumes), bleaching-agents (such as for example peroxy bleaching-agents and chlorine bleaching-agents), bleach activators, bleach stabilizers, bleach catalysts, enzymes, anti-graying inhibitors, without the ingredients being limited to these groups of substances. Frequently, important ingredients of these preparations are also detergent auxiliaries, which are understood to include in a non-limiting sense as examples, optical brighteners, UV-stabilizers, and soil repellents, i.e., polymers that counteract redeposition of dirt on the fibers. Each group of substances is defined below in more detail.

For the case where at least part of the preparations are present as molded bodies, binding auxiliaries and disintegration auxiliaries can also be comprised.

Beside the fluorine-containing non-ionic surfactants, the detergents can comprise additional non-ionic surfactants as well as anionic, zwitterionic and cationic surfactants as additional surfactants.

Exemplary suitable anionic surfactants are those of the sulfonate and sulfate type. Suitable surfactants of the sulfonate type are advantageously $C_{9-13}$-alkylbenzene sulfonates, olefin sulfonates, i.e., mixtures of alkene- and hydroxyalkane sulfonates, and disulfonates, as are obtained, for example, from $C_{12-18}$-monoolefins having a terminal or internal double bond, by sulfonation with gaseous sulfur trioxide and subsequent alkaline or acidic hydrolysis of the sulfonation products. Those alkane sulfonates, obtained from $C_{12-18}$ alkanes by sulfochlorination or sulfoxidation, for example, with subsequent hydrolysis or neutralization, are also suitable. The esters of 2-sulfofatty acids (ester sulfonates), e.g. the 2-sulfonated methyl esters of hydrogenated coco-, palm nut- or tallow acid, are likewise suitable.

Further suitable anionic surfactants are sulfated fatty acid esters of glycerin. They include the mono-, di- and triesters and also mixtures of them, such as those obtained by the esterification of a monoglycerin with 1 to 3 moles fatty acid or the transesterification of triglycerides with 0.3 to 2 moles glycerin. Preferred sulfated fatty acid esters of glycerol in this case are the sulfated products of saturated fatty acids with 6 to 22 carbon atoms, for example caproic acid, caprylic acid, capric acid, myristic acid, lauric acid, palmitic acid, stearic acid or behenic acid.

Preferred alk(en)yl sulfates are the alkali and especially sodium salts of the sulfuric acid half-ester derived from the $C_{12}$-$C_{18}$ fatty alcohols, for example from coconut butter alcohol, tallow alcohol, lauryl, myristyl, cetyl or stearyl alcohol or from $C_{10}$-$C_{20}$ oxo alcohols and those half-esters of secondary alcohols of these chain lengths. Additionally preferred are alk(en)yl sulfates of the said chain lengths, which contain a synthetic, straight-chained alkyl group produced on a petrochemical basis, which show similar degradation behavior to the suitable compounds based on fat chemical raw materials. In detergents and cleansing agents, the $C_{12}$-$C_{16}$-alkyl sulfates and $C_{12}$-$C_{15}$-alkyl sulfates and $C_{14}$-$C_{15}$ alkyl sulfates are preferred. The 2,3-alkyl sulfates, which are manufactured according to the U.S. Pat. No. 3,234,258 or 5,075,041, and which can be obtained from Shell Oil Company under the trade name DAN®, are also suitable anionic surfactants.

Sulfuric acid mono-esters derived from straight-chained or branched $C_{7-21}$ alcohols ethoxylated with 1 to 6 moles ethylene oxide are also suitable, for example 2-methyl-branched $C_{9-11}$ alcohols with an average of 3.5 moles ethylene oxide (EO) or $C_{12-18}$ fatty alcohols with 1 to 4 EO. Due to their high foaming performance, they are only used in fairly small quantities in detergents and cleansing agents, for example in amounts of 1 to 5% by weight.

Other suitable anionic surfactants are the salts of alkylsulfosuccinic acid, which are also referred to as sulfosuccinates or esters of sulfosuccinic acid, and the monoesters and/or di-esters of sulfosuccinic acid with alcohols, preferably fatty alcohols and especially ethoxylated fatty alcohols.

Preferred sulfosuccinates contain $C_{8-18}$ fatty alcohol groups or mixtures of them. Especially preferred sulfosuccinates contain a fatty alcohol residue derived from the ethoxylated fatty alcohols that are under consideration as non-ionic surfactants (see description below). Once again the especially preferred sulfosuccinates are those, whose fatty alcohol residues are derived from ethoxylated fatty alcohols with narrow range distribution. It is also possible to use alk(en)ylsuccinic acid with preferably 8 to 18 carbon atoms in the alk(en)yl chain, or salts thereof.

Soaps in particular can be considered as further anionic surfactants. Saturated fatty acid soaps are suitable, such as the salts of lauric acid, myristic acid, palmitic acid, stearic acid, hydrogenated erucic acid and behenic acid, and especially soap mixtures derived from natural fatty acids such as coconut oil fatty acid, palm kernel oil fatty acid or tallow fatty acid.

Anionic surfactants, including soaps may be in the form of their sodium, potassium or ammonium salts or as soluble salts of organic bases, such as mono-, di- or triethanolamine. The sodium or potassium salts are preferred, particularly the sodium salts. The surfactants can also be employed in the form of their magnesium salts.

In the context of the present invention, those agents are preferred that comprise 5 to 50 wt. %, preferably 7.5 to 40 wt. % and particularly 15 to 25 wt. % of one or a plurality of anionic surfactants.

Beside the fluorinated non-ionic surfactants, the detergents can comprise additional non-ionic surfactants such as for example alkoxylated, advantageously ethoxylated, particularly primary alcohols preferably containing 8 to 18 carbon atoms and, on average, 1 to 12 moles of ethylene oxide (EO) per mole of alcohol, in which the alcohol radical may be linear or preferably methyl-branched in the 2-position or may contain linear and methyl-branched radicals in the form of the mixtures typically present in oxoalcohol groups. Particularly preferred are, however, alcohol ethoxylates with linear groups from alcohols of natural origin with 12 to 18 carbon atoms, e.g. from coco-, palm-, tallow- or oleyl alcohol, and an average of 2 to 8 EO per mol alcohol. Exemplary preferred ethoxylated alcohols include $C_{12-14}$-alcohols with 3 EO or 4EO, $C_{9-11}$-alcohols with 7 EO, $C_{13-15}$-alcohols with 3 EO, 5 EO, 7 EO or 8 EO, $C_{12-18}$-alcohols with 3 EO, 5 EO or 7 EO and mixtures thereof, as well as mixtures of $C_{12-14}$-alcohols with 3 EO and $C_{12-18}$-alcohols with 5 EO. The cited degrees of ethoxylation constitute statistically average values that can be a whole or a fractional number for a specific product. Preferred alcohol ethoxylates have a narrowed homolog distribution (narrow range ethoxylates, NRE). In addition to these non-ionic surfactants, fatty alcohols with more than 12 EO can also be used. Examples of these are tallow fatty alcohol with 14 EO, 25 EO, 30 EO or 40 EO.

Another class of preferred non-ionic surfactants which may be used, either as the sole non-ionic surfactant or in combination with other non-ionic surfactants are alkoxylated, preferably ethoxylated or ethoxylated and propoxylated fatty acid alkyl esters preferably containing 1 to 4 carbon atoms in the alkyl chain, in particular fatty acid methyl esters.

A further class of non-ionic surfactants which can be advantageously used includes the alkyl polyglycosides (APG). Suitable alkyl polyglycosides satisfy the general formula $RO(G)_z$ where R is a linear or branched, particularly 2-methyl-branched, saturated or unsaturated aliphatic group containing 8 to 22 and preferably 12 to 18 carbon atoms and G stands for a glycose unit containing 5 or 6 carbon atoms, preferably glucose. The degree of glycosidation z is between 1.0 and 4.0 and preferably between 1.0 and 2.0 and particularly between 1.1 and 1.4.

Linear alkyl polyglucosides are preferably employed, that is alkyl polyglycosides, in which the polyglycosyl group is a glucose group and the alkyl group is an n-alkyl group.

Preferably, the inventive surfactant-containing preparations can comprise alkyl polyglycosides, wherein the APG contents of the preparations intended for the detergent applications, rinse applications or cleansing applications are preferably greater than 0.2 wt. %, based on the total preparation. Particularly preferred preparations comprise APG in amounts of 0.2 to 10 wt. %, advantageously in amounts of 0.2 to 5 wt. % and particularly in amounts of 0.5 to 3 wt. %.

Non-ionic surfactants of the amine oxide type, for example N-cocoalkyl-N,N-dimethylamine oxide and N-tallow alkyl- N,N-dihydroxyethylamine oxide, and the fatty acid alkanolamides may also be suitable. The quantity in which these non-ionic surfactants are used is preferably no more than the quantity in which the ethoxylated fatty alcohols are used and, particularly no more than half that quantity.

Other suitable surfactants are polyhydroxyfatty acid amides corresponding to the Formula (I),

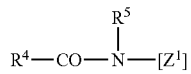
(I)

in which $R^4CO$ stands for an aliphatic acyl group with to 6 to 22 carbon atoms, $R^5$ for hydrogen, an alkyl or hydroxyalkyl group with 1 to 4 carbon atoms and $[Z^1]$ for a linear or branched polyhydroxyalkyl group with 3 to 10 carbon atoms and 3 to 10 hydroxyl groups. The polyhydroxyfatty acid amides are known substances, which may normally be obtained by reductive amination of a reducing sugar with ammonia, an alkylamine or an alkanolamine and subsequent acylation with a fatty acid, a fatty acid alkyl ester or a fatty acid chloride.

The group of polyhydroxyfatty acid amides also includes compounds corresponding to the Formula (II),

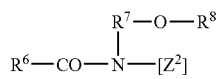
(II)

in which $R^6$ is a linear or branched alkyl or alkenyl group containing 7 to 12 carbon atoms, $R^7$ is a linear, branched or cyclic alkyl group or an aryl group containing 2 to 8 carbon atoms and $R^8$ is a linear, branched or cyclic alkyl group or an aryl group or an oxyalkyl group containing 1 to 8 carbon atoms, $C_{1-4}$-alkyl or $C_{1-4}$-phenyl groups being preferred, and $[Z^2]$ is a linear polyhydroxyalkyl group, of which the alkyl chain is substituted by at least two hydroxyl groups, or alkoxylated, preferably ethoxylated or propoxylated derivatives of that group.

$[Z^2]$ is preferably obtained by reductive amination of a reduced sugar, for example glucose, fructose, maltose, lactose, galactose, mannose or xylose. The N-alkoxy- or N-aryloxy-substituted compounds may then, for example, be converted into the required polyhydroxyfatty acid amides, as is described in WO-A-95/07331, by reaction with fatty acid methyl esters in the presence of an alkoxide as catalyst.

Furthermore, it can be preferred to also employ cationic surfactants in addition to anionic and non-ionic surfactants.

In particular, cationic surfactants should be cited as textile softeners. Examples of cationic surfactants are especially quaternary ammonium compounds, cationic polymers and emulsifiers.

Suitable examples are quaternary ammonium compounds of Formulas (III) and (IV)

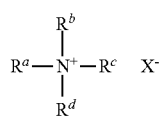
(III)

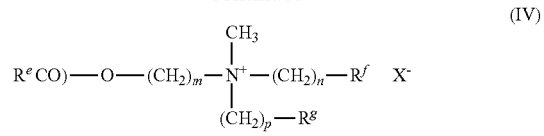
(IV)

wherein in (IV) $R^a$ and $R^b$ stand for an acyclic alkyl group having 12 to 24 carbon atoms, $R^c$ stands for a saturated $C_1$-$C_4$ alkyl or hydroxyalkyl group, $R^d$ is either equal to $R^a$, $R^b$ or $R^c$ or stands for an aromatic group. $X^-$ stands either for a halide ion, methosulfate ion, methophosphate ion or phosphate ion as well as their mixtures. Exemplary cationic compounds of Formula (III) are didecyl dimethyl ammonium chloride, ditallow dimethyl ammonium chloride or dihexadecyl ammonium chloride.

Compounds of Formula (IV) are so-called esterquats. Esterquats are characterized by their outstanding biodegradability. Here, $R^e$ stands for an aliphatic alkyl group with 12 to 22 carbon atoms and 0, 1, 2 or 3 double bonds, $R^f$ stands for H, OH or $O(CO)R^h$, $R^g$, independently of $R^f$ stands for H, OH or $O(CO)R^i$, wherein $R^h$ and $R^i$, independently of each other, each stand for an aliphatic alkyl group having 12 to 22 carbon atoms with 0, 1, 2 or 3 double bonds, m, n and p independently of each other can each have the value 1, 2 or 3. $X^-$ can be either a halide ion, methosulfate ion, methophosphate ion or phosphate ion as well as their mixtures. Preferred compounds comprise a group $O(CO)R^h$ for $R^f$ and alkyl groups with 16 to 18 carbon atoms for $R^e$ and $R^h$. Particularly preferred are compounds in which $R^g$ stands moreover for OH. Examples of compounds of Formula (IV) are methyl-N-(2-hydroxyethyl)-N,N-di(tallowacyl-oxyethyl) ammonium methosulfate, bis(palmitoyl)-ethyl-hydroxyethyl-methyl-ammonium methosulfate or methyl-N,N-bis(acyloxyethyl)-N-(2-hydroxyethyl)ammonium methosulfate. When quaternized compounds of Formula (IV) are used that have unsaturated alkyl chains, then acyl groups are preferred, whose corresponding fatty acids have an iodine number between 5 and 80, preferably between 10 and 60 and particularly between 15 and 45 and which have a cis/trans isomer ratio (in wt. %) of greater than 30:70, preferably greater than 50:50 and particularly greater than 70:30. Commercial examples are the methylhydroxyalkyl-dialkoyloxyalkylammonium methosulfates marketed by Stepan under the trade name Stepantex® or known products from Cognis with the trade name Dehyquart® or the known products manufactured by Goldschmidt-Witco under the name Rewoquat®. Further preferred compounds are the diesterquats of Formula (V), which are available under the names Rewoquat® W 222 LM or CR 3099 and which assure stability and color protection in addition to softness.

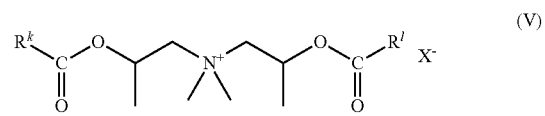
(V)

$R^k$ and $R^l$ stand, independently of each other, each for an aliphatic group having 12 to 22 carbon atoms with 0, 1, 2 or 3 double bonds.

Besides the above described quaternary compounds, other known compounds can also be employed, such as, for example quaternary imidazolinium compounds of Formula (VI),

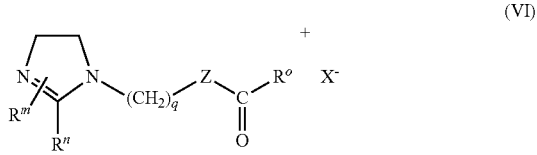

wherein R''' stands for a saturated alkyl group with 1 to 4 carbon atoms, R'' and R°, independently of each other, each stand for an aliphatic, saturated or unsaturated alkyl group with 12 to 18 carbon atoms, R'' can alternatively stand for $O(CO)R^p$, wherein $R^p$ means an aliphatic, saturated or unsaturated alkyl group with 12 to 18 carbon atoms, and Z means an NH group or oxygen and $X^-$ is an anion; q can assume whole numbered values between 1 and 4.

Additional suitable quaternary compounds are described by Formula (VII),

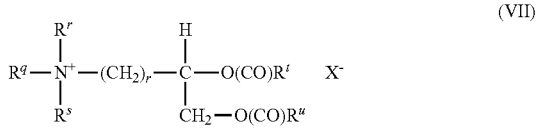

wherein $R^q$, $R^r$ and $R^s$ independently of one another stand for a $C_{1-4}$-alkyl-, alkenyl- or hydroxyalkyl-group, $R^t$ and $R^u$, each independently selected, represent a $C_{8-28}$-alkyl group and r is a number between 0 and 5.

Besides the compounds of Formulae (III) to (VII), short chain, water-soluble, quaternary ammonium compounds can also be employed, such as trihydroxyethylmethylammonium methosulfate or the alkyltrimethylammonium chlorides, dialkyldimethylammonium chlorides and trialkylmethylammonium chlorides, e.g., cetyltrimethylammonium chloride, stearyltrimethylammonium chloride, distearyldimethylammonium chloride, lauryldimethylammonium chloride, lauryldimethylbenzylammonium chloride and tricetylmethylammonium chloride.

Protonated alkylamine compounds that exhibit a softening action, as well as the non-quaternary, protonated precursors of the cationic emulsifiers are also suitable.

The quaternized protein hydrolyzates illustrate further inventively usable cationic compounds.

Suitable cationic polymers include the polyquaternium polymers such as those in the CTFA Cosmetic Ingredient Dictionary (The Cosmetic, Toiletry and Fragrance Association, 1997), particularly those polyquaternium-6, polyquaternium-7, polyquaternium-10 polymers also .described as Merquats (Ucare Polymer IR 400; Amerchol), polyquaternium-4-copolymers, such as graft copolymers with a cellulosic backbone and quaternary ammonium groups that are bonded through allyl dimethyl ammonium chloride, cationic cellulose derivatives like cationic guar, such as guar hydroxypropyl triammonium chloride, and similar quaternized guar derivatives (e.g. Cosmedia Guar, manufactured by Cognis GmbH), cationic quaternary sugar derivatives (cationic alkyl polyglucosides), e.g., the commercial product Glucquat® 100, according to CTFA nomenclature a "Lauryl Methyl Gluceth-10 Hydroxypropyl Dimonium Chloride", copolymers of PVP and dimethylamino methacrylate, copolymers of vinyl imidazole and vinyl pyrrolidone, aminosilicone polymers and copolymers.

Polyquaternized polymers (e.g., Luviquat Care from BASF) and also cationic biopolymers based on chitin and its derivatives, for example the polymer obtained under the trade name Chitosan® (manufacturer: Cognis) can also be employed.

Cationic silicone oils, such as, for example, the commercially available products Q2-7224 (manufacturer: Dow Corning; a stabilized trimethylsilylamodimethicone), Dow Corning® 929 emulsion (comprising a hydroxylamino-modified silicone, also referred to as amodimethicone), SM-2059 (manufacturer: General Electric), SLM-55067 (manufacturer: Wacker), and Abil®-Quat 3270 and 3272 (manufacturer: Goldschmidt-Rewo; diquaternary polydimethylsiloxanes, Quaternium-80), as well as siliconequat Rewoquat® SQ 1 (Tegopren® 6922, manufacturer: Goldschmidt-Rewo) are similarly suitable according to the invention.

Compounds of Formula (VIII) are likewise usable,

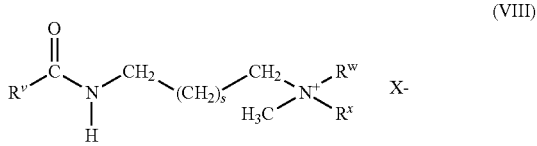

which can be alkylamido amines in their non-quaternary form or, as shown, in their quaternary form. $R^v$ can be an aliphatic acyl group having 12 to 22 carbon atoms with 0, 1, 2 or 3 double bonds, s can assume values between 0 and 5. $R^w$ and $R^x$ stand, independently of one another, each for H, $C_{1-4}$-alkyl or hydroxyalkyl. Preferred compounds are fatty acid amido amines such as stearylamidopropyl dimethylamine, available under the trade name Tego Amid®S 18, or 3-tallowamidopropyl trimethyl ammonium methosulfate, available under the trade name Stepantex® X 9124, which are characterized by their good conditioning action as well as by their color transfer inhibiting action and particularly by their good biodegradability.

If cationic surfactants are employed, then they are preferably comprised in the preparations in amounts of 0.01 to 10 wt. %, particularly 0.1 to 3.0 wt. %.

In the inventive agents, the total surfactant content lies between 5 and 50 wt. %, preferably between 10 and 35 wt. %.

Beside the surfactants, builders are the most important ingredients of detergents and cleansing agents. The inventive surfactant-containing preparations may contain any of the builders typically used in detergents and cleansing agents, i.e., in particular, zeolites, silicates, carbonates, organic co-builders and also (where there are no ecological reasons preventing their use) phosphates.

Suitable crystalline, layer forming sodium silicates correspond to the general formula $NaMSi_xO_{2x+1}\cdot H_2O$, wherein M is sodium or hydrogen, x is a number from 1.9 to 4 and y is a number from 0 to 20, preferred values for x being 2, 3 or 4. These types of crystalline layered silicates are described, for example, in the European Patent application EP-A-0 164 514. Preferred crystalline layered silicates of the given formula are those in which M stands for sodium and x assumes the values 2 or 3. Both β- and δ-sodium disilicate $Na_2Si_2O_5yH_2O$ are particularly preferred, wherein β-sodium silicate can be obtained for example from the process described in the International Patent application WO-A-91/08171.

Other useful builders are amorphous sodium silicates with a modulus ($Na_2O:SiO_2$ ratio) of 1:2 to 1:3.3, preferably 1:2 to 1:2.8 and more preferably 1:2 to 1:2.6, which dissolve with a delay and exhibit multiple wash cycle properties. The delay in dissolution compared with conventional amorphous sodium silicates can have been obtained in various ways, for example by surface treatment, compounding, compressing/compacting or by over-drying. This type of X-ray amorphous silicates, which similarly possess a delayed dissolution in comparison with the customary water glasses, are described, for example in the German Patent application DE-A44 00 024. The products have microcrystalline regions between 10 and a few hundred nm in size, values of up to at most 50 nm and especially up to at most 20 nm being preferred. Compacted/densified amorphous silicates, compounded amorphous silicates and over dried X-ray-amorphous silicates are particularly preferred.

Of the optionally suitable fine crystalline, synthetic zeolites containing bound water, zeolite A and/or P are preferred. A particularly preferred zeolite P is zeolite MAP (e.g., commercial product DOUCIL A24 from Crosfield). However, the zeolites X as well as mixtures of A, X and/or P are also suitable. Commercially available and preferred in the context of the present invention is, for example, also a co-crystallizate of zeolite X and zeolite A (ca. 80 wt. % zeolite X), which is marketed under the name of VEGOBOND AX® by Condea Augusta S.p.A. and which can be described by the formula

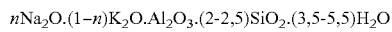

$n\text{Na}_2\text{O}.(1-n)\text{K}_2\text{O}.\text{Al}_2\text{O}_3.(2-2,5)\text{SiO}_2.(3,5-5,5)\text{H}_2\text{O}$ Suitable zeolites have a mean particle size of less than 10 μm (volume distribution, as measured by the Coulter Counter Method) and comprise preferably 18 to 22% by weight and more preferably 20 to 22% by weight of bound water.

Naturally, the generally known phosphates can also be added to the detergents as builders, in so far that their use should not be avoided on ecological grounds. The sodium salts of the orthophosphates, the pyrophosphates and especially the tripolyphosphates are particularly suitable.

Useful organic builders are, for example, the polycarboxylic acids usable in the form of their sodium salts, polycarboxylic acids in this context being understood to be carboxylic acids that carry more than one acid function. These include, for example, citric acid, adipic acid, succinic acid, glutaric acid, malic acid, tartaric acid, maleic acid, fumaric acid, sugar acids, aminocarboxylic acids, nitrilotriacetic acid (NTA), providing its use is not ecologically unsafe, and mixtures thereof. Preferred salts are the salts of polycarboxylic acids such as citric acid, adipic acid, succinic acid, glutaric acid, tartaric acid, sugar acids and mixtures thereof. Acids per se can also be used. Besides their building action, the acids also typically have the property of an acidifying component and, hence also serve to establish a lower and milder pH of surfactant-containing preparations according to the invention. Citric acid, succinic acid, glutaric acid, adipic acid, gluconic acid and any mixtures thereof are particularly mentioned in this regard.

Polymeric polycarboxylates are also suitable as builders. They are for example the alkali metal salts of polyacrylic or polymethacrylic acid, for example those with a relative molecular weight of 500 to 70,000 g/mol.

The molecular weights mentioned in the context of the present invention for polymeric polycarboxylates are weight-average molecular weights $M_w$ of the particular acid form which, fundamentally, were determined by gel permeation chromatography (GPC), using a UV detector. The measurement was carried out against an external polyacrylic acid standard, which provides realistic molecular weight values by virtue of its structural similarity to the polymers investigated. These values differ distinctly from the molecular weights measured against polystyrene sulfonic acids as standard. The molecular weights measured against polystyrene acids are generally significantly higher than the molecular weights mentioned in the context of the present invention.

Particularly suitable polymers are polyacrylates, which preferably have a molecular weight of 2000 to 20,000 g/mol. By virtue of their superior solubility, preferred representatives of this group are again the short-chain polyacrylates, which have molecular weights of 2000 to 10,000 g/mol and, more particularly, 3000 to 5000 g/mol.

In addition, copolymeric polycarboxylates are suitable, particularly those of acrylic acid with methacrylic acid or of acrylic acid or methacrylic acid with maleic acid. Copolymers of acrylic acid with maleic acid, which comprise 50 to 90 wt. % acrylic acid and 50 to 10 wt. % maleic acid, have proven to be particularly suitable. Their relative molecular weight, based on free acids, generally ranges from 2000 to 70,000 g/mol, preferably 20,000 to 50,000 g/mol and especially 30,000 to 40,000 g/mol.

The (co)polymeric polycarboxylates can be added either as powders or as aqueous solutions. The (co)polymeric polycarboxylate content in the inventive detergents and cleansing agents is advantageously 0.5 to 20 wt. %, particularly 3 to 10 wt. %.

In order to improve the water solubility, the polymers can also comprise allyl sulfonic acids, allyloxy benzenesulfonic acid and methallyl sulfonic acid as the monomer.

Particular preference is also given to biodegradable polymers comprising more than two different monomer units, examples being those comprising, as monomers, salts of acrylic acid and of maleic acid, and also vinyl alcohol or vinyl alcohol derivatives, or salts of acrylic acid and of 2-alkylallyl sulfonic acid, and also sugar derivatives.

Further preferred copolymers are those which preferably contain acrolein and acrylic acid/acrylic acid salts or acrolein and vinyl acetate as monomers.

Similarly, other preferred builders are polymeric aminodicarboxylic acids, salts or precursors thereof. Particularly preferred are those polyaspartic acids or their salts and derivatives that have, to some extent, a bleach-stabilizing action in addition to cobuilder properties.

Further preferred builders are polyacetals that can be obtained by treating dialdehydes with polyol carboxylic acids, and which possess 5 to 7 carbon atoms and at least 3 hydroxyl groups. Preferred polyacetals are obtained from dialdehydes like glyoxal, glutaraldehyde, terephthalaldehyde as well as their mixtures and from polycarboxylic acids like gluconic acid and/or glucoheptonic acid.

Further suitable organic builders are dextrins, for example oligomers or polymers of carbohydrates that can be obtained by the partial hydrolysis of starches. The hydrolysis can be carried out using typical processes, for example acidic or enzymatic catalyzed processes. The hydrolysis products preferably have average molecular weights in the range 400 to 500,000 g/mol. A polysaccharide with a dextrose equivalent (DE) of 0.5 to 40 and, more particularly, 2 to 30 is preferred, the DE being an accepted measure of the reducing effect of a polysaccharide by comparison with dextrose, which has a DE of 100. Both maltodextrins with a DE between 3 and 20 and dry glucose syrups with a DE between 20 and 37 and also so-called yellow dextrins and white dextrins with relatively high molecular weights of 2000 to 30,000 g/mol may be used. A preferred dextrin is described in the British Patent application 94 19 091.

The oxidized derivatives of such dextrins are their products of reaction with oxidizing agents that are capable of oxidizing at least one alcohol function of the saccharide ring to the carboxylic acid function. An oxidized oligosaccharide is also suitable, wherein a product oxidized at $C_6$ of the saccharide ring can be particularly advantageous.

Oxydisuccinates and other derivatives of disuccinates, preferably ethylenediamine disuccinate are also further suitable cobuilders. Ethylenediamine-N,N'-disuccinate (EDDS) is preferably used here in the form of the sodium or magnesium salt. In this context, glycerin disuccinates and glycerin trisuccinates are also preferred. Suitable addition quantities in zeolite-containing and/or silicate-containing formulations range from 3 to 15% by weight.

Other useful organic co-builders are, for example, acetylated hydroxycarboxylic acids and salts thereof which may optionally be present in lactone form and which contain at least 4 carbon atoms, at least one hydroxyl group and at most two acid groups.

Phosphonates represent a further class of substances with cobuilder properties. In particular, they are hydroxyalkane phosphonates or aminoalkane phosphonates. Among the hydroalkane phosphonates, 1-hydroxyethane-1,1-diphosphonate (HEDP) is a particularly important cobuilder. It is normally added as its sodium salt, the disodium salt reacting neutral and the tetrasodium salt reacting alkaline (pH=9). Ethylenediamine tetramethylene phosphonate (EDTMP), diethylenetriamine pentamethylene phosphonate (DTPMP) and their higher homologs are preferably chosen as aminoalkane phosphonates. They are preferably employed in the form of their neutral-reacting sodium salts, e.g., as the hexasodium salt of EDTMP or as the hepta and octasodium salt of DTPMP. Of the phosphonates, HEDP is preferably used as the builder. The aminoalkane phosphonates additionally possess a pronounced ability to complex heavy metals. Accordingly, it can be preferred, particularly where the inventive surfactant-containing preparations also comprise bleach, to use aminoalkane phosphonates, particularly DTPMP, or mixtures of the mentioned phosphonates.

In addition, any compounds capable of forming complexes with alkaline earth metal ions may be used as the co-builder.

Among the compounds, which serve as bleaching agents and liberate $H_2O_2$ in water, sodium perborate tetrahydrate and sodium perborate monohydrate are of particular importance. Examples of further bleaching agents that may be employed are sodium percarbonate, peroxypyrophosphates, citrate perhydrates and $H_2O_2$-liberating peracidic salts or peracids, such as perbenzoates, peroxyphthalates, diperoxyazelaic acid, phthaloimino peracid or diperoxydodecanedioic acid. If cleansing or bleaching agent preparations are manufactured for automatic dishwashers, then bleaching agents from the group of organic bleaching agents may also be employed. Typical organic bleaching agents are the diacyl peroxides, such as, e.g., dibenzoyl peroxide. Further typical organic bleaching agents are the peroxy acids, wherein the alkylperoxy acids and the arylperoxy acids may be named as examples. Preferred representatives that can be added are (a) peroxybenzoic acid and ring-substituted derivatives thereof, such as alkyl peroxybenzoic acids, but also peroxy-α-naphthoic acid and magnesium monoperphthalate, (b) aliphatic or substituted aliphatic peroxy acids, such as peroxylauric acid, peroxystearic acid, ε-phthalimidoperoxycaproic acid [phthaloiminoperoxyhexanoic acid (PAP)], o-carboxybenzamido peroxycaproic acid, N-nonenylamido peradipic acid and N-nonenylamido persuccinates and (c) aliphatic and araliphatic peroxydicarboxylic acids, such as 1,12-diperoxycarboxylic acid, 1,9-diperoxyazelaic acid, diperoxysebacic acid, diperoxybrassylic acid, diperoxyphthalic acids, 2-decyldiperoxybutane-1,4-dioic acid, and N,N-terephthaloyl-di (6-aminopercaproic acid).

The surfactant-containing preparations can comprise bleach activators in order to achieve an improved bleaching action on washing or cleaning at temperatures of 60° C. and below. Bleach activators, which can be used are compounds which, under perhydrolysis conditions, yield aliphatic peroxycarboxylic acids having preferably 1 to 10 carbon atoms, in particular 2 to 4 carbon atoms, and/or optionally substituted perbenzoic acid. Substances, which carry O-acyl and/or N-acyl groups of said number of carbon atoms and/or optionally substituted benzoyl groups, are suitable. Preference is given to polyacylated alkylenediamines, in particular tetraacetyl ethylenediamine (TAED), acylated triazine derivatives, in particular 1,5-diacetyl-2,4-dioxohexahydro-1,3,5-triazine (DADHT), acylated glycolurils, in particular tetraacetyl glycoluril (TAG U), N-acylimides, in particular N-nonanoyl succinimide (NOSI), acylated phenol sulfonates, in particular n-nonanoyl- or isononanoyloxybenzene sulfonate (n- or iso-NOBS), carboxylic acid anhydrides, in particular phthalic anhydride, acylated polyhydroxy alcohols, in particular triacetin, ethylene glycol diacetate and 2,5-diacetoxy-2,5-dihydrofuran.

In addition to, or instead of the conventional bleach activators mentioned above, so-called bleach catalysts may also be incorporated into the surfactant-containing preparations. These substances are bleach-boosting transition metal salts or transition metal complexes such as, for example, manganese-, iron-, cobalt-, ruthenium- or molybdenum-salen or -carbonyl complexes. Manganese, iron, cobalt, ruthenium, molybdenum, titanium, vanadium and copper complexes with nitrogen-containing tripod ligands, as well as cobalt-, iron-, copper- and ruthenium-ammine complexes may also be employed as the bleach catalysts.

Suitable enzymes are those from the classes of proteases, lipases, amylases, cellulases or mixtures thereof. Enzymatic active materials obtained from bacterial sources or fungi such as *bacillus subtilis, bacillus licheniformis* and *streptomyceus griseus* are particularly well suited. Proteases of the subtilisin type and particularly proteases that are obtained from *bacillus lentus*, are preferably used. Here, mixtures of enzymes are of particular interest, for example protease and amylase or protease and lipase or protease and cellulase or cellulase and lipase or protease, amylase and lipase or protease, lipase and cellulase, in particular, however, cellulase-containing mixtures. Peroxidases or oxidases have also proved to be suitable in certain cases. The enzymes can be adsorbed on carriers and/or embedded in cladding substances, in order to protect them against premature decomposition. The content of the enzymes, enzyme mixtures or enzyme granulates in the inventive surfactant-containing preparations can be, for example, about 0.1 to 5% by weight and is preferably 0.1 to about 2% by weight.

A preferred group of suitable additives are optical brighteners. The optical brighteners that are usually used in detergents can be used here. Examples of optical brighteners are derivatives of diaminostilbene disulfonic acid or its alkali metal salts. Suitable optical brighteners are, for example, salts of 4,4'-bis-(2-anilino-4-morpholino-1,3,5-triazinyl-6-amino) stilbene-2,2'-disulfonic acid or compounds of similar structure which contain a diethanolamino group, a methylamino group, an anilino group or a 2-methoxyethylamino group instead of the morpholino group. Brighteners of the substituted diphenylstyryl type may also be comprised in the part portions (wash active preparations) of the inventive surfactant-containing preparations, for example the alkali salts of 4,4'-bis-(2-sulfostyryl)diphenyl, 4,4'-bis(4-chloro-3-sulfostyryl)diphenyl or 4-(4-chlorostyryl)-4'-(2-sulfostyryl)diphenyl. Mixtures of the mentioned brighteners may also be used.

A further inventively preferred group of additives are UV-protection substances. UV absorbers can become attached to the treated textiles and improve the light stability of the fibers and/or the light stability of the various ingredients of the formulation. UV-absorbers are understood to mean organic compounds (light-protective filters) that are able to absorb ultra violet radiation and emit the absorbed energy in the form of longer wavelength radiation, for example as heat. Compounds, which possess these desired properties, are for example, the efficient radiationless deactivating compounds and derivatives of benzophenone having substituents in position(s) 2- and/or 4. Also suitable are substituted benzotriazoles, such as for example the water-soluble monosodium salt of 3-(2H-benzotriazole-2-yl)-4-hydroxy-5-(methylpropyl) benzenesulfonic acid (Cibafast® H), acrylates, which are phenyl-substituted in position 3 (cinnamic acid derivatives) optionally with cyano groups in position 2, salicylates, organic Nickel complexes, as well as natural substances such as umbelliferone and the endogenous urocanic acid. The biphenyl derivatives and above all the stilbene derivatives such as, for example, those described in EP 0728749 A and commercially available as Tinosorb® FD or Tinosorb® FR from Ciba, are of particular importance. As UV-B absorbers can be cited: 3-benzylidenecamphor or 3-benzylidenenorcamphor and its derivatives, for example 3-(4-methylbenzylidene) camphor, as described in EP 0693471 B1; 4-aminobenzoic acid derivatives, preferably the 2-ethylhexyl ester of 4-(dimethylamino)benzoic acid, the 2-octyl ester of 4-(dimethylamino)benzoic acid, and the amyl ester of 4-(dimethylamino)benzoic acid; esters of cinnamic acid, preferably the 2-ethylhexyl ester of 4-methoxycinnamic acid, the propyl ester of 4-methoxycinnamic acid, the isoamyl ester of 4-methoxycinnamic acid, the 2-ethylhexyl ester of 2-cyano-3,3-phenylcinnamic acid, (Octocrylene); esters of salicylic acid, preferably the 2-ethylhexyl ester of salicylic acid, the 4-isopropylbenzyl ester of salicylic acid, the homomenthyl ester of salicylic acid; derivatives of benzophenone, preferably 2-hydroxy-4-methoxybenzophenone, 2-hydroxy-4-methoxy-4'-methylbenzophenone, 2,2'-dihydroxy-4-methoxybenzophenone; esters of benzalmalonic acid, preferably the di-2-ethylhexylester of 4-methoxybenzmalonic acid; triazine derivatives, such as, for example 2,4,6-trianilino-(p-carbo-2'-ethyl-1'-hexyloxy)-1,3,5-triazine and octyl triazone, as described in EP 0818450 A1 or dioctyl butamidotriazone (Uvasorb® HEB); propane-1,3-diones, such as for example 1-(4-tert.-butylphenyl)-3-(4'-methoxyphenyl)propane-1,3-dione; and ketotricyclo(5.2.1.0)decane derivatives, such as are described in EP 0694521 B1. Further suitable are 2-phenylbenzimidazole-5-sulfonic acid and its alkali-, alkaline earth-, ammonium-, alkylammonium-, alkanolammonium- and glucammonium salts; sulfonic acid derivatives of benzophenones, preferably 2-hydroxy-4-methoxybenzophenone-5-sulfonic acid and its salts; sulfonic acid derivatives of 3-benzylidenecamphor, such as for example 4-(2-oxo-3-bornylidenemethyl)benzene sulfonic acid and 2-methyl-5-(2-oxo-3-bornylidene) sulfonic acid and its salts. Typical UV-A filters particularly include derivatives of benzoylmethane, such as, for example 1-(4'-tert.-butylphenyl)-3-(4'-methoxyphenyl)propane-1,3-d ione, 4-tert.-butyl-4'-methoxydibenzoyl methane (PARSOL 1789), 1-phenyl-3-(4'-isopropylphenyl)propane-1,3-dione as well as enamine compounds, as described in DE 19712033 A1 (BASF). Naturally, the UV-A and UV-B filters can also be added as mixtures. Beside the cited soluble materials, insoluble, light-protecting pigments, namely finely dispersed, preferably, nano metal oxides or salts can also be considered for this task. Exemplary suitable metal oxides are particularly zinc oxide and titanium oxide and also oxides of iron, zirconium, silicon, manganese, aluminum and cerium as well as their mixtures. Silicates (talc), barium sulfate or zinc stearate can be added as salts. The oxides and salts are already used in the form of pigments for skin care and skin protecting emulsions and decorative cosmetics. Here, the particles should have a mean diameter of less than 100 nm, preferably between 5 and 50 nm and especially between 15 and 30 nm. They can be spherical, however elliptical or other shaped particles can also be used. The pigments can also be surface treated, i.e., hydrophilized or hydrophobized. Typical examples are coated titanium dioxides, such as, for example Titandioxid T 805 (Degussa) or Eusolex® T2000 (Merck). Hydrophobic coating agents preferably include silicones and among them specifically trialkoxyoctylsilanes or simethicones. Micronized zinc oxide is preferably used. Further suitable UV light protection filters may be found in the review by P. Finkel in SoFW-Journal, Volume 122 (1996), p. 543.

The UV absorbers are normally employed in amounts of 0.01 wt. % to 5 wt. %, preferably from 0.03 wt. % to 1 wt. %.

A further inventively preferred group of additives are colorants, particularly water-soluble or water-dispersible colorants. Colorants, which are typically employed to improve the optical impression, are preferred in the inventive detergents, rinse agents, cleansing agents and textile treatment agents. Preferred colorants are not difficult for the person skilled in the art to choose, particularly as these types of common colorants have a high storage stability, are not affected by the other ingredients of the wash active preparations or by light and do not have any pronounced substantivity for the textile fibers being treated, so as not to color them. According to the invention, the colorants are inventively present in the detergents and/or cleansing agents in amounts less than 0.01 wt. %.

A further class of additives that can be added to the detergents and/or cleansing agents according to the invention are polymers. Among these polymers are firstly polymers that show cobuilder properties during the washing or cleaning or rinsing, i.e. polyacrylic acids and modified polyacrylic acids or corresponding copolymers. A further group of polymers are polyvinyl pyrrolidone and other graying inhibitors, such as copolymers of polyvinyl pyrrolidone, cellulose ethers and the like. In addition, preferred polymers also include so-called soil repellents such as are described in detail below.

The detergents and cleansing agents can also comprise soil repellents as additional inventive additives, i.e. polymers that are absorbed on fibers and which positively influence the removal of oil- and fat from the textiles during the wash and therefore purposefully counteract any redeposition of dirt. This effect is particularly noticeable when a textile is dirty and had been previously already washed several times with an inventive detergent or cleansing agent that comprised this oil- or fat-removing component. The preferred oil and fat removing components include, for example, non-ionic cellulose ethers such as methyl cellulose and methyl hydroxypropyl cellulose with a content of methoxy groups of 15 to 30 wt. % and hydroxypropoxy groups of 1 to 15 wt. %, each based on the non-ionic cellulose ether, as well as polymers of phthalic acid and/or terephthalic acid or their derivatives known from the prior art, particularly polymers of ethylene terephthalates and/or polyethylene glycol terephthalates or anionically and/or non-ionically modified derivatives thereof. From these, the sulfonated derivatives of the phthalic acid polymers and the terephthalic acid polymers are particularly preferred.

Particularly in the case that the preparations are liquid or in gel form, they can also comprise solvents. Examples of suitable solvents are mono- or polyhydroxy alcohols containing 1 to 4 carbon atoms. Preferred alcohols are ethanol, 1,2-propanediol, and glycerin as well as any mixture thereof. The solvents can be comprised in the liquid preparations in an amount of 2 to 12 wt. %, based on the finished preparation.

The cited additives are added to the detergents and/or cleansing agents in amounts of up to 30 wt. %, preferably 2 to 20 wt. %.

This enumeration of ingredients in detergents and cleansing agents, which can be present in the inventive detergent, rinse agent or cleansing agent, is in no way exclusive, but rather only reflects the major typical ingredients of this type of agent. Particularly in the case that the preparations are liquid or in gel form, they can also comprise organic solvents. They are preferably mono- or polyhydroxy alcohols containing 1 to 4 carbon atoms Ethanol, 1,2-propanediol, and glycerin together with mixtures thereof are preferred alcohols in such agents. In preferred embodiments, such agents comprise 2 to 12 wt. % of such alcohols.

According to a particular embodiment, liquid or solid detergents are particularly preferred. Detergents and cleansing agents that are suitable for delicates or gentle treatment of delicate textiles are likewise particularly preferred.

In particular, textile-care products, in particular textile after-treatment agents, preferably textile conditioners, rinse-softeners or drying cloths that comprise pachouli oil, pachouli alcohol and/or derivatives thereof are also suitable.

Additional ingredients can be employed according to the desired usage. Rinse-softening compositions for the rinse-bath finishing are extensively described in the prior art. Usually, these compositions comprise a cationic quaternary ammonium compound as the active substance, which is dispersed in water. Depending on the content of the active substance in the finished softening composition, one distinguishes between diluted, ready-for-use products (active substance contents below 7 wt. %), or so-called concentrates (active substance content above 7 wt. %). Because of the lower volume and the simultaneous correspondingly lower packaging and transport costs, the textile softener concentrates demonstrate advantages from the ecological point of view and have increasingly penetrated the market. As a result of incorporating cationic compounds that are only slightly soluble in water, conventional softener compositions are in the form of dispersions, possess a milky-cloudy appearance and are not translucent. For reasons of product esthetics, it can, however, be desirable to offer the consumer transparent, clear softeners that optically stand out from the known products.

Inventive softeners advantageously comprise cationic surfactants, which were already described in detail above, as the textile softening active substance. These inventive agents particularly preferably comprise so-called esterquats. Although there are a great number of possible compounds in this substance class, according to the invention, esterquats are particularly advantageously incorporated, which can be manufactured by treating trialkanolamines with a mixture of fatty acids and dicarboxylic acids, the reaction product being optionally subsequently alkoxylated and quaternized by known methods, as is described in DE 195 39 846.

Esterquats manufactured in this manner are outstandingly suited for the manufacture of the inventive portions that can be incorporated as the softener. Given that according to the choice of the trialkanolamine, the fatty acids and the dicarboxylic acids as well as the quaternizing agent, a great number of suitable products can be manufactured and incorporated into the inventive agent, the inventively preferred incorporated esterquat is more precisely described by its manufacturing path than by the presentation of a general formula.

The cited components, which react with one another to afford the preferred usable esterquats, can be employed in varying weight ratios to one another. In the scope of the present invention, softeners are preferred, in which a reaction product of trialkanolamines with a mixture of fatty acids and dicarboxylic acids in the molar ratio 1:10 to 10:1, preferably 1:5 to 5:1, was optionally alkoxylated and then quaternized in a known manner, is comprised in amounts of 2 to 60, preferably 3 to 35 and particularly 5 to 30 wt. %. The use of triethanolamine is particularly preferred here, such that further preferred softeners of the present invention comprise a reaction product of triethanolamine with a mixture of fatty acids and dicarboxylic acids in the molar ratio 1:10 to 10:1, preferably 1:5 to 5:1, that was optionally alkoxylated and then quaternized in a known manner, in amounts of 2 to 60, preferably 3 to 35 and particularly 5 to 30 wt. %.

Any acid obtained from vegetal or animal oils and fats can be used as the fatty acid in the reaction mixture to manufacture the esterquat. Thus, to all intents and purposes, a non-solid at room temperature, i.e. pasty to liquid fatty acid, can be employed as the fatty acid in the reaction mixture.

Independently of their physical state, the fatty acids can be saturated or mono- to polyunsaturated. Of course, not only "pure" fatty acids can be used, but also the industrial fatty acid mixtures, obtained by cleaving fats and oils, these mixtures being once again distinctly preferred on economical grounds.

Thus the reaction mixtures for the manufacture of the esterquat for the inventive clear aqueous softener can incorporate, for example, individual species or mixtures of the following acids: caprylic acid, pelargonic acid, capric acid, lauric acid, myristic acid, palmitic acid, stearic acid, octadecan-12-ol-oic acid, arachinic acid, behenic acid, lignoceric acid, ceroticu acid, melissic acid, 10-undecenic acid, petroselic acid, petroselaidic acid, oleic acid, elaidic acid, ricinoleic acid, linolaidic acid, α- and β-eleosteraic acid, gadoleic acid, erucaic acid, and/or brassidic acid. Naturally, the fatty acids with an odd number of carbon atoms can also be employed, for example undecanoic acid, tridecanoic acid, pentadecanoic acid, heptadecanoic acid, nonadecanoic acid, heneicosanoic acid, tricosanoic acid, pentacosanoic acid, and/or heptacosanoic acid.

In the context of the present invention, the use of fatty acids of Formula XIII in the reaction mixture for the manufacture of the esterquats is preferred, such that preferred softeners comprise a reaction product of trialkanolamines with a mixture of fatty acids of Formula IX,

$$R^1\text{—CO—OH} \qquad (IX)$$

in which $R^1$—CO— stands for an aliphatic, linear or branched acyl group with 6 to 22 carbon atoms and 0 and/or 1, 2 or 3 double bonds, and dicarboxylic acids in the molar ratio 1:10 to 10:1, preferably 1:5 to 5:1 that was optionally alkoxylated and then quaternized in a known manner, in amounts of 2 to 60, preferably 3 to 35 and particularly 5 to 30 wt. %.

Principally saturated or mono- or polyunsaturated α,ω-dicarboxylic acids come into consideration as the dicarboxylic acids that are suitable for the manufacture of the esterquat to be incorporated into the inventive agents Exemplary saturated carboxylic acids are oxalic acid, malonic acid, succinic acid, glutaric acid, adipic acid, pimelic acid, cork acid, azelaic acid, sebacic acid, undecanoic and dodecanoic acid, brassylic acid, tetra- and pentadecanoic acid, thapioic acid as well as hepta-, octa- and nonadecanoic acid, eicosanoic and heneicosanoic acid as well as phellogenoic acid. Thus, dicarboxylic acids that correspond to the general formula XIII are advantageously incorporated in the reaction mixture, such that inventive agents are preferred that comprise a reaction product of trialkanolamines with a mixture of fatty acids and dicarboxylic acids of Formula X,

HO—OC—[X]—CO—OH  (X)

in which X stands for an optionally hydroxy substituted alkylene group with 1 to 10 carbon atoms in the molar ratio 1:10 to 10:1, preferably 1:5 to 5:1 that was optionally alkoxylated and then quaternized in a known manner, in amounts of 2 to 60, preferably 3 to 35 and particularly 5 to 30 wt. % in the agents.

Among the great number of manufacturable and inventively employable esterquats, those that are particularly tried and tested are those in which the alkanolamine is triethanolamine and the dicarboxylic acid is adipic acid. Thus, in the scope of the present invention, agents are particularly preferred, that comprise a reaction product of triethanolamine with a mixture of fatty acids and adipic acid in the molar ratio 1:5 to 5:1, preferably 1:3 to 3:1, subsequently optionally alkoxylated and then quaternized in a known manner, in amounts of 2 to 60, preferably 3 to 35 and particularly 5 to 30 wt. %.

The inventive agents can be also furnished, independently of whether they are formulated as the textile detergent, detergent auxiliary or softener, with further additional benefits. For example, color transfer inhibiting compositions, 'anti-graying formula' agents, easy-iron agents, special fragrance-release agents, agents with improved dirt removal or redeposition, antibacterials, UV-protection agents etc. can be formulated. Several examples are described below:

As textile surfaces, particularly of rayon, spun rayon, cotton and their mixtures can wrinkle of their own accord because the individual fibers are sensitive to flection, bending, pressing and squeezing at right angles to the fiber direction, the inventive agents can comprise synthetic wrinkle-protection agents. These include, for example, synthetic products based on fatty acids, fatty acid esters, fatty acid amides, fatty acid alkylol esters, fatty acid alkylol amides or fatty alcohols that have been mainly treated with ethylene oxide, or products based on lecithin or modified phosphoric acid esters.

An increased wear comfort can result from the additional use of antistats that can be additionally included in the inventive agents. Antistats increase the surface conductivity and thereby allow an improved discharge of built-up charges. Generally, external antistats are substances with at least one hydrophilic molecule ligand and provide a more or less hygroscopic film on the surfaces. These mainly interface active antistats can be subdivided into nitrogen-containing (amines, amides, quaternary ammonium compounds), phosphorus-containing (phosphoric acid esters) and sulfur-containing (alkyl sulfonates, alkyl sulfates) antistats. Lauryl (or stearyl) dimethylbenzylammonium chlorides are suitable antistats for textiles or as additives to detergents, resulting in an additional finishing effect.

Silicone derivatives, for example, can be added to the inventive agents to improve the water-absorption capacity, the wettability of the treated textiles and to facilitate ironing of the treated textiles. They additionally improve the final rinse behavior of the inventive agents by their foam-inhibiting properties. Exemplary preferred silicone derivatives are polydialkylsiloxanes or alkylarylsiloxanes, in which the alkyl groups possess one to five carbon atoms and are totally or partially fluorinated. Preferred silicones are polydimethylsiloxanes that can be optionally derivatized and then be aminofunctional or quaternized or possess Si—OH, Si—H and/or SiCl bonds. The viscosities of the preferred silicones at 25° C. are in the range between 100 and 100,000 centistokes, wherein the silicones can be added in amounts between 0.2 and 5 wt. % based on the total agent.

Finally, the inventive agents can also comprise UV absorbers, which are absorbed on the treated textiles and improve the light stability of the fibers. Compounds, which possess these desired properties, are for example, the efficient radiationless deactivating compounds and derivatives of benzophenone having substituents in position(s) 2- and/or 4. Also suitable are substituted benzotriazoles, acrylates that are phenyl-substituted in position 3 (cinnamic acid derivatives), optionally with cyano groups in position 2, salicylates, organic Ni complexes, as well as natural substances such as umbelliferone and the endogenous urocanic acid.

Pharmaceutical and Cosmetic Compositions

A further subject matter of the invention is the use of nonionic surfactants in pharmaceutical and/or cosmetic compositions to reduce the adhesion of microorganisms.

The pharmaceutical compositions can be incorporated for both the treatment and also the prevention of illnesses.

For the manufacture of pharmaceutical preparations, active substances, optionally in combination with other active principals, can be incorporated with one or a plurality of inert, conventional carriers and/or diluents, e.g., with gelatin, gum arabic, corn starch, milk sugar, raw sugar, sorbitol, microcrystalline cellulose, magnesium stearate, polyvinyl pyrrolidone, citric acid, tartaric acid, water, benzyl alcohol, polyalkylene glycol, water/ethanol, water/glycerin, water/sorbitol, water/polyethylene glycol, propylene glycol, titanium dioxide, a cellulose derivative such as e.g. carboxymethyl cellulose or fat-containing substances like hydrogenated fat, talcum or vegetal oils or their appropriate mixtures, in usual galenical preparations such as tablets, dragees, capsules, powders, suspensions, drops, ampoules, juices or suppositories. Optionally, moreover, preservatives, stabilizers, wetting agents, emulsifiers or salts for modifying the osmotic pressure or buffers can be comprised. Interfacially active auxiliaries such as salts of gallic acid or animal or vegetal phospholipids, mixtures thereof as well as liposomes or their constituents can also be used as the carrier.

The inventive pharmaceutical and cosmetic preparations can also comprise, in addition to the inventive active substances, active substances that prevent the adhesion of fungi, as are described for example in WO 03/051124. Moreover, the use of the inventive active substances can be realized in combination with antimicrobials, particularly antibacterials, antimycotics and/or antiseptics and/or in combination with astringent substances.

The antimycotics are preferably those already normally used for treating fungal infections, particularly in the case of Candidoses. They can especially concern antimycotics of the polyene type, principally Nystatin, Amphotericin B or Natamycin, and/or antimycotics of the azole type, principally Miconazole, Clotrimazole or Ketokonazole. By combining with other antimycotics, the removal of the fungi can be optionally accelerated, wherein preferably a synergistic effect appears. The anti-microbials can be advantageously used in lower concentrations than was usual in previous treatments.

The astringent substances principally concern aluminum salts, phenol condensation products, (synthetic tanning agents), natural products and tanning agent-containing drugs.

In a particularly preferred embodiment according to the invention, the pharmaceutical or cosmetic preparations concern those for topical application on the skin and their adnexa and/or for application on the mucous membrane, particularly in the oral and genital region, or for intertriginous application. In the following, these preparations are designated as "skin treatment agents".

The skin treatment agent can particularly concern a lotion, a cream, a balm, a paste, an oil, a gel, a powder, a spry or aerosol, a solution, particularly alcoholic solution or tincture, a moist dressing, an occlusal dressing, a plaster, a stick preparation, a hair treatment or hair care product, particularly a hair shampoo, a hair lotion, a hair cure or a hair water, a bubble bath, a shower bath or a foot bath.

The physiological carriers of the skin treatment agents advantageously include one or in any combination, a plurality of auxiliaries as are normally used in such preparations, such as, e.g., fats, oils, greasing materials, waxes, silicones, emulsifiers, dispersants, pearlizers, alcohols, polyols, consistency agents, stabilizers, thickeners, swelling agents, hydrotropes or moisturizers and/or humectants, polymers, surfactants, plasticizers, defoamers, alkali- or acidifiers, water softeners, adsorbants, light protective agents, electrolytes, sequestering agents, organic solvents, preservatives, germicides, particularly fungicides or bactericides, antioxidants, biogenic active substances, vitamins, protein hydrolyzates, mono-, oligo- and polysaccharides, enzyme inhibitors, particularly MMP1-inhibiting substances, deodorants or odor absorbers, antiperspirants, antidandruff agents, α-hydroxy- and α-ketocarboxylic acids, fragrances, colorants and/or pigments.

The inventive skin treatment agents are advantageously presented for topical administration in the form of a liquid or solid oil-in-water emulsion, water-in-oil emulsion, multiple emulsion, micro-emulsion, PIT-emulsion or Pickering emulsion, in the form of a hydrogel, an alcoholic gel, a lipogel, in the form of a mono- or multiphase solution, a foam, a balm, a plaster, a suspension, a powder or a mixture with at least one polymer that is a suitable medicinal adhesive. The inventive skin treatment agents can also be presented in an anhydrous state, such as for example in an oil or a balsam. For this, the carrier can be a vegetable or animal oil, a mineral oil, a synthetic oil or a mixture of such oils.

In a further particularly preferred embodiment according to the invention, the cosmetic and/or pharmaceutical preparations concern those for oral application, wherein the target area of the application is the mouth. In a preferred embodiment here, one of the previously described skin treatment agents is used, wherein the composition is so chosen that the preparation concerns a mouth cream, a balm, a tincture or a suspension. The term "pharmaceutical preparation for oral application" also includes prosthesis cleansing agents, particularly cleansing agents for dentures.

Moreover, in the oral region, mouthwashes, toothpastes, tablets, particularly lozenges as well as sprays or aerosols are further preferred embodiments.

For partial dentures or dentures, the presentation is suitable both as denture cleaning tablets and also as mouth rinses or mouth water, or as toothpaste.

The inventive mouth, tooth and/or dental prostheses care agents can exist, for example, as gels, liquid toothpaste, viscous toothpaste, denture cleaners or adhesive creams for prostheses. For this, the inventively used materials must be proposed in a suitable carrier.

The inventive toothpastes and tooth gels can comprise, in addition to the inventive active substances, particularly surfactants, cleaning compounds, aromas, sweeteners as well as additional active substances known to the person skilled in the art. Water and binders advantageously serve as the carriers. Furthermore, humectants, preservatives, consistency agents and/or color pigments, for example, can also be comprised.

The inventive mouth water can involve aqueous, in particular also alcohol-containing, aromaticized concentrates or also ready-for-use solutions. In addition to the inventive active substances, the mouth waters can comprise in particular surfactants, aromas, colorants, fluorides, astringent substances, antibacterials and/or additional active substances.

In regard to the cited additional active substances that can be comprised in the oral treatment agents, they can concern, for example, a fluorine compound, an active substance against plaque bacteria, an active substance against calculus, for remineralization, against sensitive teeth or for the protection of the gums. Moreover, the additional active substance can concern an additional active substance for fungal treatment, particularly treatment of candidosis.

Additional typical additives for the mouth, tooth and/or dental prostheses care agents are, e.g.:
pH adjustors and buffer substances such as, e.g., sodium bicarbonate, sodium citrate, sodium benzoate, citric acid, phosphoric acid or acidic salts, e.g., $NaH_2PO_4$
Wound healing and anti-inflammatory substances such as, e.g., allantoin, urea, panthenol, azulene or camomile extract
Further active materials against tartar such as, e.g., organophosphonates, e.g. hydroxyethane diphosphonates or azacycloheptane diphosphonate
Preservatives such as, e.g., salts of sorbic acid, sodium benzoate, chlorhexidine digluconate, p-hydroxybenzoic acid or its esters.
Plaque-inhibitors such as, e.g., hexachlorophene, chlorhexidine, hexetidine, triclosan, bromochlorophene, or phenyl salicylate.

EXAMPLES

1. Adhesion Tests with Molds

The silicone sealant DC3390 was used. 1 wt. % of surfactant was added and homogenized in the Speedmixer. The surfactants indicated in Table 1 were tested in comparison with the joint sealing compound without the addition of the surfactants being tested. The resulting composition was spread as the film (22×22×2 mm) and left to harden in air. The resulting test specimen was disinfected with 70% ethanol for 10 minutes, then washed with distilled water and dried. The test specimens were subsequently coated with a germ suspension of *Aspergillus niger* and incubated for one hour. The germ suspension was then siphoned off and the specimen was washed twice. The specimens were transferred into sterile tubes that contained 5 ml of inactivation solution and shaken on a shaker for 10 minutes at 400 rpm. To determine the number of adhered spores, firstly the specimens were placed in sterile 6-well plates and covered with wort agar with INT, secondly a determination of the colony count of the inactivation solution was carried out by the inoculation plate method. After 48 hours incubation at 25° C., the number of colony forming units (CFU) was subsequently determined. A significant reduction in the number of colony forming units was achieved with some of the added substances (Table 1).

2. Incorporation Test with Molds

In order to examine the fungicidal activity of the substances, the incorporation test was carried out with *Aspergillus niger*. A Petri dish with a diameter of ca. 6 cm was filled with 6 ml of liquid malt extract agar (ca. 50° C.). 300 µl of each 10% surfactant-active substance solution were added and homogeneously distributed by tilting the Petri dish. Therefore, the concentration of the active substance was 0.5% in agar. Polyethylene glycol 600, polyethylene glycol 2000, polyethylene glycol dimethyl ether, EUMULGIN B1, EUMULGIN B2, MERGITAL B10, BIODAC 2/32, DEHYDOL 100, DEHYDOL LT7, DEHYPON LS54 as well as the silicic acid esters of DEHYDOL LT 7 and BIODAC 2/32 were tested. After the agar surface hardened, the surface was charged with a spore suspension of *Aspergillus niger*. The agar plates were incubated at 25° C. The assay was realized by visual determination of the growth in comparison with the control without active substance. No impairment of the growth was observed for any of the tested substances (Table 1).

TABLE 1

Results of the Adhesion Test and the Incorporation Test.

| Active substance | Description | Manufacturer | Mold adhesion [%] | Fungicide Activity |
|---|---|---|---|---|
| none | | | 100 | |
| Polyethylene glycol 600 | PEG with MW = 600 | Aldrich | 81 | + |
| Polyethylene glycol 2000 | PEG with MW = 2000 | Aldrich | 60 | + |
| Polyethylene glycol dimethyl ether | methyl terminated PEG | Aldrich | 85 | + |
| EUMULGIN B1 | C16-18 with 12 EO | Cognis | 2 | + |
| EUMULGIN B2 | C16-18 with 20 EO | Cognis | 23 | + |
| EUMULGIN B3 | C16-18 with 30 EO | Cognis | 95 | n.d. |
| MERGITAL B10 | C22 with 10 EO | Cognis | 20 | + |
| DEHYDOL LT7 | C12-18 with 7 EO | Cognis | 7 | + |
| DEHYDOL 100 | C12-18 with 9 EO | Cognis | 13 | + |
| DEHYPON LS 54 | C12-14 with 5 EO and 4 PO | Cognis | 27 | + |
| BIODAC 2/32 | C10-12 with 5 EO and 5 PO | Cognis | 8 | + |
| ZONYL FSO 100 | ethoxylated fluorosurfactant | DuPont | 5 | n.d. |
| ZONYL FSP | anionic fluorosurfactant | DuPont | 100 | n.d. |
| DYNASYLAN F8261 | perfluorinated octyltriethoxy-silane | Degussa | 80 | n.d. |
| DISPONIL NP 4 | Nonylphenol with 4 EO | Cognis | 71 | n.d. |
| DISPONIL NP 9 | Nonylphenol with 9 EO | Cognis | 17 | n.d. |
| DISPONIL NP 20 | Nonylphenol with 20 EO | Cognis | 71 | n.d. |
| DISPONIL NP 30 | Nonylphenol with 30 EO | Cognis | 98 | n.d. |
| Silicic acid ester with EUMULGIN B1 | Non-ionic surfactant-silicic acid ester | Henkel | 13 | n.d. |
| Silicic acid ester with DEHYDOL LT7 | Non-ionic surfactant-silicic acid ester | Henkel | 9 | + |
| Silicic acid ester with BIODAC 2/32 | Non-ionic surfactant-silicic acid ester | Henkel | 7 | + |

| Symbol | Assessment in the test | Assessment of the biocidal effect |
|---|---|---|
| + | growth as in control | no biocidal effect |
| 1 | slight growth inhibition | slight biocidal action |
| 2 | strong growth inhibition | stronger biocidal action |
| − | no growth | good biocidal action |
| n.d. | not carried out | |

3. Liquid detergents

| Raw material | Quantity in weight percent |
|---|---|
| $C_{12}$-$C_{18}$ Fatty alcohol + 7 EO (DEHYDOL LT 7, Cognis) | 15 |
| $C_{12}$-$C_{14}$ Fatty alcohol $C_{12}$-$C_{18}$ Fatty alcohol + 7 EO (DEHYDOL LT 7, Cognis) + 2 EO-sulfate, sodium salt (TEXAPON N 70, Cognis) | 7 |
| $C_{8-18}$-Fatty acid cut (coconut oil fatty acid, EDENOR K12-18, Cognis) | 8 |
| Sodium citrate | 1.5 |
| Enzyme | + |
| Colorant | + |
| Perfume | + |
| Non-ionic surfactant | 0.4 |
| water | ad 100 |

4. Pre-portioned liquid detergent in polyvinyl alcohol film

| Raw material | Quantity in weight percent |
|---|---|
| $C_{12-14}$-Fatty alcohol + 5-EO + 4-PO (MARLOX MO 154, Sasol) | 25 |
| Dodecylbenzene sulfonate isopropylammonium salt | 24.5 |
| $C_{8-18}$-Fatty acid cut (coconut oil fatty acid, EDENOR K12-18, Cognis) | 17.5 |
| Ethanol | 3.5 |
| Sodium citrate | 0.6 |
| Enzyme | 2.0 |
| water | 6.0 |
| Non-ionic surfactant | 0.6 |
| Colorant | + |
| Perfume | + |
| Propylene glycol | ad 100 |

The pre-portioned detergent size was 50 ml.

5. Detergent powder

| Raw material | Quantity in weight percent |
|---|---|
| $C_{10}$-$C_{13}$-Alkylbenzene sulfonate | 13.3 |
| $C_{12}$-$C_{18}$-Alkyl sulfate | 5.5 |
| $C_{12}$-$C_{18}$-Alcohol with 7 EO | 5.3 |
| $C_{12}$-$C_{18}$-Alcohol with 4.5 EO | 0.6 |
| Soil Repellent | 0.7 |
| $C_{16}$-$C_{18}$ Fatty acid (EDENOR ST1 $C_{16}$-$C_{18}$, Cognis) | 0.8 |
| Polyethylene glycol Molecular weight = 4000 g/mol | 1.8 |
| Phosphonate | 1.0 |
| Polyacrylate | 2.8 |

-continued

5. Detergent powder

| Raw material | Quantity in weight percent |
| --- | --- |
| Carboxymethylcellulose | 0.9 |
| polyvinyl pyrrolidone | 0.5 |
| Zeolite (anhydrous active substance) | 32.1 |
| Sodium carbonate | 4.5 |
| Sodium citrate | 3.6 |
| Citric acid | 3.7 |
| Sodium hydrogen carbonate | 4.9 |
| sodium sulfate | 3.8 |
| Foam inhibitor | + |
| Enzyme | + |
| Colorant | + |
| Perfume | + |
| Non-ionic surfactant | 0.4 |
| Water/salts | ad 100 |

The detergent is dosed with 75 g.

The non-ionic surfactants can also be incorporated as the ingredient of the perfume. They are then comprised in concentrations of 0.1-80 wt. % in the perfume oil and are introduced into the wash liquor through the perfume oil comprised in the detergent formulation.

What is claimed is:

1. A one component adhesive or joint sealant material that cures by reaction with moisture and comprising a curable polymer, wherein said material further comprises one or more non-ionic surfactants and/or has been treated with one or more non-ionic surfactants; wherein the one or more non-ionic surfactants are selected from an addition product of ethylene oxide (EO) units on a fatty alcohol consisting of a linear, $C_{14-20}$ primary alcohol with 10 to 22 ethylene oxide (EO) units; silicic acid esters of the addition product of ethylene oxide (EO) units on a fatty alcohol consisting of a linear, $C_{14-20}$ primary alcohol with 10 to 22 ethylene oxide (EO) units; an addition product of ethylene oxide (EO) units on a fatty alcohol, consisting of a linear, $C_{10-20}$ primary alcohol with 5 to 11 eth lene oxide EO units; silicic acid esters of the addition product of ethylene oxide (EO) units on a fatty alcohol, consisting of a linear, $C_{10-20}$ primary alcohol with 5 to 11 ethylene oxide (EO) units; an addition product of ethylene oxide (EO) units and propylene oxide units on a fatty alcohol consisting of a linear, $C_{10-16}$ primary alcohol with 3 to 7 EO units and 2 to 6 PO units; silicic acid esters of the addition product of ethylene oxide (EO) units and propylene oxide units on a fatty alcohol consisting of a linear $C_{10-16}$ primary alcohol with 3 to 7 EO units and 2 to 6 PO units; and combinations thereof, wherein the one or more non-ionic surfactants are in carrier-bound form.

2. The material according to claim 1, wherein the one or more non-ionic surfactants are in carrier-bound form and are silicic acid esters.

3. The material according to claim 2, wherein the one or more silicic acid esters of non-ionic surfactants include one or more silicic acid esters of ethoxylated compounds having a degree of ethoxylation of 5 to 15.

4. The material according to claim 1, wherein the one or more non-ionic surfactants include one or more non-ionic surfactants selected from the group consisting of ethoxylated and propoxylated compounds.

5. The material according to claim 1, wherein the non-ionic surfactants are present in said material in an amount of up to 20 wt. %.

6. The material of claim 1 wherein the one or more non-ionic surfactants are selected from an addition product of ethylene oxide (EO) units on a fatty alcohol consisting of a linear, $C_{16-18}$ primary alcohol with 11 to 13 ethylene oxide (EO) units; silicic acid esters of the addition product of ethylene oxide (EO) units on a fatty alcohol consisting of a linear, $C_{16-18}$ primary alcohol with 11 to 13 ethylene oxide (EO) units; an addition product of ethylene oxide (ED) units on a fatty alcohol, consisting of a linear, $C_{12-18}$ primary alcohol with 6 to 8 ethylene oxide (EO) units; silicic acid esters of the addition product of ethylene oxide (ED) units on a fatty alcohol, consisting of a linear, $C_{12-18}$ primary alcohol with 6 to 8 ethylene oxide (EO) units; an addition product of ethylene oxide (EO) units and propylene oxide units on a fatty alcohol consisting of a linear, $C_{10-12}$ primary alcohol with 4 to 6 EO units and 4 to 6 PO units is; silicic acid esters of the addition product of ethylene oxide (EO) units and propylene oxide units on a fatty alcohol consisting of a linear, $C_{10-12}$ primary alcohol with 4 to 6 EO units and 4 to 6 PO units is; and combinations thereof.

7. The material of claim 1 wherein the one or more non-ionic surfactants are selected from an addition product of ethylene oxide (EO) units on a fatty alcohol consisting of a linear, $C_{16-18}$ primary alcohol with 12 ethylene oxide (EO) units; silicic acid esters of the addition product of ethylene oxide (EO) units on a fatty alcohol consisting of a linear, $C_{16-18}$ primary alcohol with 12 ethylene oxide (EO) units; an addition product of ethylene oxide (EO) units on a fatty alcohol, consisting of a linear, $C_{12-18}$ primary alcohol with 7 ethylene oxide (ED) units; silicic acid esters of the addition product of ethylene oxide (EO) units on a fatty alcohol, consisting of a linear, $C_{12-18}$ primary alcohol with 7 ethylene oxide (EO) units; an addition product of ethylene oxide (EO) units and propylene oxide units on a fatty alcohol consisting of a linear, $C_{10-12}$ primary alcohol with 5 EO units and 5 PO units is; silicic acid esters of the addition product of ethylene oxide (EO) units and propylene oxide units on a fatty alcohol consisting of a linear, $C_{10-12}$ primary alcohol with 5 EO units and 5 PO units is; and combinations thereof.

8. The material according to claim 1, wherein the moisture curable polymer is a moisture curable urethane polymer.

9. Cured reaction products of the moisture curable material of claim 1.

10. The material according to claim 1, wherein the moisture curable polymer is a moisture curable silicone polymer.

11. The material according to claim 1, wherein the polymer is a moisture curable silicone RTV polymer.

12. The material according to claim 1 comprising cured reaction products of a moisture curable silicone polymer.

13. The material according to claim 1 further comprising at least one of a catalyst or crosslinker.

14. The material according to claim 1 further comprising a catalyst.

15. Cured reaction products of a one component adhesive or joint sealant material that cures by reaction with moisture and comprising a curable polymer, wherein the cured reaction products have a surface treated with one or more non-ionic surfactants, and the one or more non-ionic surfactants are non-covalently bonded to said surface, wherein the one or more non-ionic surfactants are selected from an addition product of ethylene oxide (EO) units on a fatty alcohol consisting of a linear, $C_{14-20}$ primary alcohol with 10 to 22 ethylene oxide (EO) units; silicic acid esters of the addition product of ethylene oxide (EO) units on a fatty alcohol consisting of a linear, $C_{14-20}$ primary alcohol with 10 to 22 ethylene oxide (EO) units; an addition product of ethylene oxide (EO) units on a fatty alcohol, consisting of a linear, $C_{10-20}$ primary alcohol with 5 to 11 eth lene oxide (EO) units; silicic acid esters of the addition product of ethylene oxide (EO)

units on a fatty alcohol, consisting of a linear, $C_{10-20}$ primary alcohol with 5 to 11 ethylene oxide (EO) units; an addition product of ethylene oxide (EO) units and propylene oxide units on a fatty alcohol consisting of a linear, $C_{10-16}$ primary alcohol with 3 to 7 EO units and 2 to 6 PO units; silicic acid esters of the addition product of ethylene oxide (EO) units and propylene oxide units on a fatty alcohol consisting of a linear, $C_{10-16}$ primary alcohol with 3 to 7 EO units and 2 to 6 PO units; and combinations thereof.

16. The material according to claim 15, wherein the one or more non-ionic surfactants are deposited on the a surface of said cured reaction products in a concentration sufficiently low such that the one or more non-ionic surfactants act neither biocidally nor biostatically.

17. The material according to claim 15 further comprising at least one of a catalyst or crosslinker.

18. The material according to claim 15, wherein the one or more non-ionic surfactants include one or more non-ionic surfactants selected from the group consisting of ethoxylated and propoxylated compounds.

19. The material of claim 15 wherein the one or more non-ionic surfactants are selected from an addition product of ethylene oxide (EO) units on a fatty alcohol consisting of a linear, $C_{16-18}$ primary alcohol with 11 to 13 ethylene oxide (EO) units; silicic acid esters of the addition product of ethylene oxide (EO) units on a fatty alcohol consisting of a linear, $C_{16-18}$ primary alcohol with 11 to 13 ethylene oxide (EO) units; an addition product of ethylene oxide (EO) units on a fatty alcohol, consisting of a linear, $C_{12-18}$ primary alcohol with 6 to 8 ethylene oxide (EO) units; silicic acid esters of the addition product of ethylene oxide (EO) units on a fatty alcohol, consisting of a linear, $C_{12-18}$ primary alcohol with 6 to 8 ethylene oxide (EO) units; an addition product of ethylene oxide (EO) units and propylene oxide units on a fatty alcohol consisting of a linear, $C_{10-12}$ primary alcohol with 4 to 6 EO units and 4 to 6 PO units is; silicic acid esters of the addition product of ethylene oxide (EO) units and propylene oxide units on a fatty alcohol consisting of a linear, $C_{10-12}$ primary alcohol with 4 to 6 ED units and 4 to 6 PO units is; and combinations thereof.

20. The material of claim 15 wherein the one or more non-ionic surfactants are selected from an addition product of ethylene oxide (EO) units on a fatty alcohol consisting of a linear, $C_{16-18}$ primary alcohol with 12 ethylene oxide (ED) units; silicic acid esters of the addition product of ethylene oxide (EO) units on a fatty alcohol consisting of a linear, $C_{16-18}$ primary alcohol with 12 ethylene oxide (EO) units; an addition product of ethylene oxide (EO) units on a fatty alcohol, consisting of a linear, $C_{12-18}$ primary alcohol with 7 ethylene oxide (EO) units; silicic acid esters of the addition product of ethylene oxide (EO) units on a fatty alcohol, consisting of a linear, $C_{12-18}$ primary alcohol with 7 ethylene oxide (EO) units; an addition product of ethylene oxide (EO) units and propylene oxide units on a fatty alcohol consisting of a linear, $C_{10-12}$ primary alcohol with 5 EO units and 5 PO units is; silicic acid esters of the addition product of ethylene oxide (EO) units and propylene oxide units on a fatty alcohol consisting of a linear, $C_{10-12}$ primary alcohol with 5 EO units and 5 PO units is; and combinations thereof.

* * * * *